(12) United States Patent
Butler

(10) Patent No.: US 11,510,642 B2
(45) Date of Patent: Nov. 29, 2022

(54) SPATIOTEMPORAL RECONSTRUCTION IN HIGHER DIMENSIONS OF A MOVING VASCULAR PULSE WAVE FROM A PLURALITY OF LOWER DIMENSIONAL ANGIOGRAPHIC PROJECTIONS

(71) Applicant: William E. Butler, Boston, MA (US)

(72) Inventor: William E. Butler, Boston, MA (US)

( * ) Notice: Subject to any disclaimer, the term of this patent is extended or adjusted under 35 U.S.C. 154(b) by 49 days.

(21) Appl. No.: 16/784,125

(22) Filed: Feb. 6, 2020

(65) Prior Publication Data

US 2020/0245965 A1 Aug. 6, 2020

Related U.S. Application Data

(60) Provisional application No. 62/801,766, filed on Feb. 6, 2019.

(51) Int. Cl.
*G06K 9/00* (2022.01)
*A61B 6/00* (2006.01)
(Continued)

(52) U.S. Cl.
CPC ............ *A61B 6/5288* (2013.01); *A61B 6/504* (2013.01); *G06T 7/0016* (2013.01); *G06T 15/08* (2013.01);
(Continued)

(58) Field of Classification Search
CPC ....... A61B 6/5288; A61B 6/504; A61B 5/318; A61B 5/031; A61B 5/14552;
(Continued)

(56) References Cited

U.S. PATENT DOCUMENTS 3,335,716 A   8/1967  Alt et al.
5,628,980 A   5/1997  Ranganathan et al.
(Continued)

FOREIGN PATENT DOCUMENTS

CN   101406392 B   5/2011
EP     1322219 B1   5/2007
(Continued)

OTHER PUBLICATIONS

International Search Report and Written Opinion received in related application No. PCT/US20/17057, dated May 7, 2020 (7 pages).

(Continued)

*Primary Examiner* — Atiba O Fitzpatrick
(74) *Attorney, Agent, or Firm* — Edell, Shapiro & Finnan, LLC

(57) ABSTRACT

A plurality of image projections are acquired at faster than cardiac rate. A spatiotemporal reconstruction of cardiac frequency angiographic phenomena in three spatial dimensions is generated from two dimensional image projections using physiological coherence at cardiac frequency. Complex valued methods may be used to operate on the plurality of image projections to reconstruct a higher dimensional spatiotemporal object. From a plurality of two spatial dimensional angiographic projections, a 3D spatial reconstruction of moving pulse waves and other cardiac frequency angiographic phenomena is obtained. Reconstruction techniques for angiographic data obtained from biplane angiography devices are also provided herein.

19 Claims, 16 Drawing Sheets

RAW SPACE ANGIOGRAMS

ARTERIAL ROI

VENOUS ROI

(51) Int. Cl.
*G06T 15/08* (2011.01)
*G06T 7/00* (2017.01)
*A61B 5/1455* (2006.01)
*A61B 5/03* (2006.01)
*A61B 5/318* (2021.01)

(52) U.S. Cl.
CPC ........... *A61B 5/031* (2013.01); *A61B 5/14552* (2013.01); *A61B 5/318* (2021.01); *A61B 6/4078* (2013.01); *A61B 6/4085* (2013.01); *A61B 6/481* (2013.01); *G06T 2207/10116* (2013.01); *G06T 2207/30012* (2013.01); *G06T 2207/30104* (2013.01)

(58) Field of Classification Search
CPC ..... A61B 6/4078; A61B 6/4085; A61B 6/481; G06T 7/0016; G06T 15/08; G06T 2207/10116; G06T 2207/30012; G06T 2207/30104
See application file for complete search history.

(56) References Cited

U.S. PATENT DOCUMENTS

| | | | |
|---|---|---|---|
| 5,637,871 A | 6/1997 | Piety et al. | |
| 5,963,676 A | 10/1999 | Wu et al. | |
| 6,195,456 B1 | 2/2001 | Balasubramanian et al. | |
| 6,442,414 B1 | 8/2002 | Watanabe | |
| 6,549,801 B1 | 4/2003 | Chen et al. | |
| 6,842,638 B1 | 1/2005 | Suri et al. | |
| 6,975,753 B2 | 12/2005 | Matsuura et al. | |
| 6,985,632 B2 | 1/2006 | Sato et al. | |
| 7,020,314 B1 | 3/2006 | Suri et al. | |
| 7,035,679 B2 | 4/2006 | Addison et al. | |
| 7,201,892 B2 | 4/2007 | Achilefu et al. | |
| 7,359,062 B2 | 4/2008 | Chen et al. | |
| 7,602,183 B2 | 10/2009 | Lustig et al. | |
| 8,244,334 B2 | 8/2012 | Huang et al. | |
| 8,306,295 B2 | 11/2012 | Bruder et al. | |
| 8,306,303 B2 | 11/2012 | Bruder et al. | |
| 8,417,048 B2 | 4/2013 | Reboni et al. | |
| 8,559,692 B2 | 10/2013 | Reboni et al. | |
| 8,605,976 B2 | 12/2013 | Diamant et al. | |
| 8,611,633 B2 | 12/2013 | Kwon et al. | |
| 8,628,751 B2 | 1/2014 | Neumann et al. | |
| 8,948,480 B2 | 2/2015 | Liu et al. | |
| 9,019,305 B2 | 4/2015 | Baumgart et al. | |
| 9,036,780 B2 | 5/2015 | Kyriakou et al. | |
| 9,165,349 B2 | 10/2015 | Kwon et al. | |
| 9,324,005 B2 | 4/2016 | Wadhwa et al. | |
| 9,345,413 B2 | 5/2016 | Schie et al. | |
| 9,357,916 B2 | 6/2016 | Srivastava et al. | |
| 9,811,901 B2 | 11/2017 | Wu et al. | |
| 9,814,384 B2 | 11/2017 | Schmoll | |
| 9,836,849 B2 | 12/2017 | Dickrell, III et al. | |
| 9,962,124 B2 | 5/2018 | Najarian et al. | |
| 10,123,761 B2 | 11/2018 | Butler | |
| 10,226,176 B2 | 3/2019 | Schmoll | |
| 10,299,677 B2 | 5/2019 | Spaide | |
| 10,653,379 B2 | 5/2020 | Rapoport | |
| 11,386,563 B2 | 7/2022 | Figueroa-Alvarez et al. | |
| 2004/0101090 A1 | 5/2004 | Drummond et al. | |
| 2005/0080327 A1 | 4/2005 | Jenkins et al. | |
| 2007/0106146 A1* | 5/2007 | Altmann | A61B 6/5247 600/407 |
| 2007/0106149 A1 | 5/2007 | Mistretta | |
| 2007/0185393 A1 | 8/2007 | Zhou et al. | |
| 2008/0045847 A1 | 2/2008 | Farag et al. | |
| 2008/0226149 A1 | 9/2008 | Wischmann et al. | |
| 2010/0113949 A1 | 5/2010 | Sathyanarayana | |
| 2010/0272184 A1 | 10/2010 | Fishbain et al. | |
| 2011/0040178 A1 | 2/2011 | Brunner et al. | |
| 2011/0142288 A1 | 6/2011 | Diamant et al. | |
| 2012/0134553 A1 | 5/2012 | Liao et al. | |
| 2013/0101187 A1 | 4/2013 | Sundar et al. | |
| 2013/0116554 A1 | 5/2013 | Kaiser et al. | |
| 2013/0243348 A1 | 9/2013 | Goshen et al. | |
| 2014/0005563 A1 | 1/2014 | Ramanathan et al. | |
| 2014/0044330 A1 | 2/2014 | Klingenbeck | |
| 2014/0072190 A1 | 3/2014 | Wu et al. | |
| 2014/0072228 A1 | 3/2014 | Rubinstein et al. | |
| 2014/0072229 A1 | 3/2014 | Wadhwa et al. | |
| 2014/0378795 A1 | 12/2014 | McKenna | |
| 2015/0045684 A1 | 2/2015 | Schie | |
| 2015/0190533 A1 | 7/2015 | Newton et al. | |
| 2015/0257653 A1 | 9/2015 | Hyde et al. | |
| 2016/0135775 A1 | 5/2016 | Mistretta et al. | |
| 2016/0189394 A1 | 6/2016 | Zhang et al. | |
| 2016/0220112 A1 | 8/2016 | Schmoll | |
| 2016/0267704 A1 | 9/2016 | Mistretta et al. | |
| 2016/0349346 A1 | 12/2016 | Cheng | |
| 2017/0000441 A1 | 1/2017 | Butler | |
| 2017/0367603 A1 | 12/2017 | Spector | |
| 2018/0047160 A1 | 2/2018 | Wu et al. | |
| 2018/0055471 A1 | 3/2018 | Redel | |
| 2019/0015061 A1 | 1/2019 | Liebeskind et al. | |
| 2019/0046147 A1 | 2/2019 | Butler | |
| 2019/0053780 A1 | 2/2019 | Song et al. | |
| 2019/0159707 A1 | 5/2019 | Albuquerque et al. | |
| 2019/0343383 A1 | 11/2019 | Spaide | |
| 2020/0193597 A1 | 6/2020 | Fan et al. | |
| 2020/0245961 A1 | 8/2020 | Butler | |
| 2020/0245965 A1 | 8/2020 | Butler | |
| 2020/0286237 A1 | 9/2020 | Butler | |
| 2020/0305822 A1 | 10/2020 | Butler | |
| 2020/0320710 A1 | 10/2020 | Butler | |
| 2020/0397396 A1 | 12/2020 | Butler | |
| 2021/0137634 A1 | 5/2021 | Lang | |

FOREIGN PATENT DOCUMENTS

| | | |
|---|---|---|
| JP | 2002-505437 A | 2/2002 |
| JP | 2005-062147 A | 3/2005 |
| JP | 2008-006083 A | 1/2008 |
| JP | 2009-112532 A | 5/2009 |
| JP | 2016-101364 A | 6/2016 |
| WO | 99/44503 A1 | 9/1999 |
| WO | 2006/038166 A2 | 4/2006 |
| WO | 2012-011014 A1 | 1/2012 |
| WO | 2014/162741 A1 | 10/2014 |
| WO | 2020163614 A1 | 8/2020 |
| WO | 2020163629 A1 | 8/2020 |
| WO | 2020185706 A1 | 9/2020 |
| WO | 2020198592 A1 | 10/2020 |
| WO | 2020206430 A1 | 10/2020 |

OTHER PUBLICATIONS

Zhao et al., Ultrasound Contrast Imaging Based on a Novel Algorithm Combined Pulse Inversion with Wavelet Transform, Ultrasound in Medicine & Biology, 2011, vol. 37, No. 8, pp. 1292-1305.
Faubel et al., Cilia-based flow network in the brain ventricles, Neurophysiology, Jul. 8, 2016, vol. 353, iss. 6295, pp. 176-178.
Marshall et al., Cilia orientation and the fluid mechanics of development, Current Opinion in Cell Biology, 2008, vol. 20(1), pp. 48-52.
Ohata et al., Mechanosensory Genes Pkd1 and Pkd2 Contribute to the Planar Polarization of Brain Ventricular Epithelium, The Journal of Neuroscience, Aug. 5, 2015, vol. 35(31), pp. 11153-11168.
Jalalvand et al., Ciliated neurons lining the central canal sense both fluid movement and pH through ASIC3, Nature Communications, Jan. 8, 2016, pp. 1-12.
Wagshul et al., Resonant and notch behavior in intracranial pressure dynamics, J Neurosurgery Pediatrics, May 2009, vol. 3(5), pp. 354-364.
Park et al., Alterations of pulsation absorber characteristics in experimental hydrocephalus, J Neurosurg Pediatrics, Aug. 2010, vol. 6(2), pp. 159-170.
Kotelnikov, On the transmission capacity of the "ether" and of cables in electrical communication, Proceedings of the first All-

(56) References Cited

OTHER PUBLICATIONS

Union Conference on the technological reconstruction of the communications sector and low-current engineering, Moscow 1933, vol. 1, pp. 1-23.
Sagel et al., Gated computed tomography of the human heart, Investigative radiology, Nov.-Dec. 1977, vol. 12, iss. 6, pp. 563-566.
Sarode et al., Video Motion Magnification Using Spatio-Temporal Algorithm, International Journal of Computer Applications (0975-8887), Jun. 2014, vol. 96, No. 9, pp. 9-13.
Zhao et al., Phase-Resolved Optical Coherence Tomography and Optical Doppler Tomography for Imaging Blood Flow in Human Skin with Fast Scanning Speed and High Velocity Sensitivity, Optics Letters, Jan. 15, 2000, vol. 25, iss. 2, pp. 114-116.
Yazdanfar et al., High Resolution Imaging of In vivo Cardiac Dynamics Using color Doppler Optical Coherence Tomography, Optics Express, Dec. 22, 1997, vol. 1, No. 13, pp. 424-431.
Wu et al., Eulerian Video Magnification for Revealing Subtle Changes in the World, ACM Transactions on Graphics, Jul. 1, 2012, vol. 31, iss. 4, pp. 1-8.
Wang et al., Phase-Sensitive Optical Coherence Elastography for Mapping Tissue Microstains in Real Time, Applied Physics Letter, 2007, vol. 90, pp. 164105-1-164105-3.
Robles et al., Assessing Hemoglobin Concentration Using Spectroscopic Optical Coherence Tomography for Feasibility of Tissue Diagnostics, Biomedical Optics Express, Aug. 2, 2010, vol. 1, No. 1, pp. 310-317.
Lahiri et al., Medical Applications of Infrared Thermography: A Review, Infrared Physics & Technology, 2012, vol. 55, pp. 221-235.
Mourant et al., Hemoglobin Parameters from Diffuse Reflectance Data, Journal of Biomedical Optics, Mar. 2014, vol. 19, iss. 3, pp. 037004-1-037004-9.
Makita et al., Optical Coherence Angiography, Optics Express, Aug. 21, 2006, vol. 14, No. 17, pp. 7821-7840.
Chen et al., Noninvasive Imaging of in vivo blood flow velocity using optical Doppler tomography, Optics Letters, Jul. 15, 1997, vol. 22, No. 14, pp. 1119-1121.
Izatt et al., In vivo bidirectional color Doppler flow imaging of picoliter blood volumes using optical coherence tomography, Optics Letters, Sep. 15, 1997, vol. 22, No. 18, pp. 1439-1441.
Drexler, Ultrahigh-Resolution Optical Coherence Tomography, Journal of Biomedical Optics, Jan./Feb. 2004, vol. 9, iss. 1, pp. 47-74.
Devor et al., Frontiers in optical imaging of cerebral blood flow and metabolism, Journal of Cerebral Blood Flow & Metabolism, 2012, vol. 32, pp. 1259-1276.
Chen et al., Optical Doppler Tomography, IEEE Journal on Selected Topics in Quantum Electronics, Jul. 1, 1999, vol. 5, No. 4, pp. 1134-1142.
Bachmann et al., Fluorescence Spectroscopy of Biological Tissues—A Review, Applied Spectroscopy Reviews, 2006, vol. 41, pp. 575-590.
Desmettre et al., Fluorescence Properties and Metabolic Features of Indocyanine Green (ICG) as Related to Angiography, Survey of Ophthalmology, Jul.-Aug. 2000, vol. 45, No. 1, pp. 15-27.
Martin et al., Hydrodynamic and longitudinal impedance analysis of cerebrospinal fluid dynamics at the craniovertebral junction in type I Chiari malformation, PloS One, Oct. 2013, vol. 8, iss. 10, pp. 1-9.
Nielsen, Conditions for A Class of Entanglement Transformations, Aug. 17, 1999, pp. 1-4 (Cornell University Archive, arXiv No. quant-ph/9811053v2).
Novotny et al., A Method of Photographing Fluorescence in Circulating Blood in the Human Retina, Circulation, vol. XXIV, Jul. 1961, pp. 82-86.
Pewsey et al., Circular Statistics in R, Oxford University Press, (2013) Chapters 1-3, 7 and Appendix (80 pages).
Pfister et al., Molecular diagnostics of CNS embryonal tumors, Acta Neuropathology, Nov. 2010, vol. 120, No. 5, pp. 553-566.
Pollock, Dyadic Wavelets Analysis, (2016) pp. 1-26.
Qian et al., High Resolution Stationary Digital Breast Tomosynthesis using Distributed Carbon Nanotube X-ray Source Array, Medical Physics, (Apr. 2012) vol. 39, No. 4, pp. 2090-2099.
Rashid-Farrokhi et al., Wavelet-Based Multiresolution Local Tomography, IEEE Transactions on Image Processing, Oct. 1997, vol. 6, No. 10, pp. 1412-1430.
Rollins et al., Real-time in vivo color Doppler optical coherence tomography, Journal of Biomedical Optics, Jan. 2002, vol. 7, No. 1, pp. 123-129.
Ronneberger et al., U-Net: Convolutional Networks for Biomedical Image Segmentation, May 18, 2015, pp. 1-8 (Cornell University Archive, arXiv No. 1505.04597v1).
Ruzhansky, Introduction to pseudo-differential operators, Jan. 21, 2014, pp. 1-54.
Sadowsky, The Continuous Wavelet Transform: A Tool for Signal Investigation and Understanding, John Hopkins APL Technical Digest, 1994, vol. 15, No. 4, pp. 306-318.
Saito et al., Efficient Gene Transfer into the Embryonic Mouse Brain Using in Vivo Electroporation, Developmental Biology, 2001, vol. 240, pp. 237-246.
Sen et al., 3D ROI Image Reconstruction from Truncated Computed Tomogrpahy, IEEE Transactions on Medical Imaging, May 26, 2013, pp. 1-24.
Shen et al., Growth hormone therapy and risk of recurrence/ progression in intracranial tumors: a meta-analysis, Neurol Sci, 2015, vol. 36, pp. 1859-1867.
Shy et al., X-Y separable pyramid steerable scalable kernels, (1994) pp. 237-244 (https://authors.library.caltech.edu/3438/1/SHYcvpr94.pdf).
Valens, A Really Friendly Guide to Wavelets, 1999, pp. 1-19.
Vrhel et al., Fast Computation of the Continuous Wavelet Transform through Oblique Projections, (1996) pp. 1-4 (http://citeseerx.ist.psu.edu/viewdoc/download?doi=10.1.1.66.3780&rep=rep1&type=pdf).
Wang et al., Three dimensional optical angiography, Optics Express, Apr. 2, 2007, vol. 15, No. 7, pp. 4083-4097.
Wang et al., Doppler optical micro-angiography for volumetric imaging of vascular perfusion in vivo, May 25, 2009, Optics Express, vol. 17, No. 11, pp. 8926-8940.
Wunsch, Microlocal Analysis and Evolution Equations: Lecture Notes from 2008 CMI/ETH Summer School, 2012 (92 pages).
Yang et al., The X-Ray Transform Projection of 3D Mother Wavelet Function, Research Article, Computational and Mathematical Methods in Medicine, 2013, Article ID 754829, 9 pages.
Zhu et al., Endothelial nitric oxide synthase: a potential therapeutic target for cerebrovascular diseases, Molecular Brain, 2016, vol. 9, No. 30, pp. 1-8.
Zhuang et al., Fan-beam and cone-beam image reconstruction via filtering the backprojection image of differentiated projection data, Institute of Physics Publishing, Physics in Medicine and Biology, 2004, vol. 49, pp. 5489-5503.
Taylor et al., Molecular subgroups of medulloblastoma: the current consensus, Consensus Paper, Acta Neuropathol, 2012, vol. 123, pp. 465-472.
Thavavel et al., Regularized Computed Tomography using Complex Wavelets, International Journal of Magnetic Resonance Imaging, 2007, vol. 01, No. 01, pp. 027-032.
Thielen et al., Ultrafast dynamic computed tomography myelography for the precise identification of high-flow cerebrospinal fluid leaks caused by spiculated spinal osteophytes, J Neurosurg Spine, Clinical Article, Mar. 2015, vol. 22, pp. 324-331.
Spaide et al., Retinal Vascular Layers Imaged by Fluorescein Angiography and Optical Coherence Tomography Angiography, Original investigation, JAMA Opthalmology, Jan. 2015, vol. 133, No. 1, pp. 45-50.
Ren et al., Phase-resolved functional optical coherence tomography: simultaneous imaging of in situ tissue structure, blood flow velocity, standard deviation, birefirngence, and Stokes vectors in human skin, Optics Letters, Oct. 1, 2002, vol. 27, No. 19, pp. 1702-1704.
Shenoi, Introduction to Digital Signal Processing and Filter Design, Wiley, 2006, Chapters 3-5 (217 pages).
Srinivasan et al., Quantitative Cerebral Blood Flow with Optical Coherence Tomography, Optics Express, Feb. 1, 2010, vol. 18, No. 3, pp. 2477-2494.
Steane, An introduction to spinors, Dec. 13, 2013, pp. 1-23 (Cornell University Archive, arXiv No. 1312.3824v1).

(56) References Cited

OTHER PUBLICATIONS

Thompson et al., Prognostic Value of Medulloblastoma Extent of Resection After Accounting for Molecular Subgroup: A Retrospective Integrated Clinical and Molecular Analysis, Lancet Oncol. Apr. 2016, vol. 17, No. 4, pp. 484-495.
Timmons, Image-Guided Neurosurgery: Integration of Medical Image Data with a Real-time View of the Surgical Field, Jun. 1997, pp. 1-66.
Tran et al., Learning Spatiotemporal Features with 3D Convolutional Networks, Proceedings of the 2015 IEEE International Conference on Computer Vision (ICCV), (2015) pp. 4489-4497.
Rao et al., Shear strain imaging using shear deformations (2008) Med. Phys. 35(2):412-423.
Weaver et al., Brain mechanical property measurement using MRE with intrinsic activation Phys. Med. Biol. (2012) 57:7275-7287.
Kashif et al., Model-Based Noninvasive Estimation of Intracranial Pressure from Cerebral Blood Flow Velocity and Arterial Pressure, Sci. Transl. Med. (2012) vol. 4, No. 129, pp. 1-10.
Bayer et al., Two-Dimensional Simulations of Displacement Accumulation Incorporating Shear Strain, Ultrason. Imaging (2014) vol. 36(1):55-73.
Feingold et al., Quantitative volumetric perfusion mapping of the microvasculature using contrast ultrasound, Invest Radiol. (2010) 45:669-674.
Johnson et al., Local mechanical properties of white matter structures in the human brain, NeuroImage (2013) 79:145-152.
Khullar et al., Wavelet-based fMRI analysis: 3-D denoising, signal seperation, and validation metrics, NeuroImage (2011) 54:2867-2884.
Lee et al., Wavelet Methods for Inverting the Radon Transform with Noisy Data, IEEE Transactions on Image Processing, (2001) vol. 10, No. 1, pp. 79-94 (16 pages) (https://www.math.purdue.edu/~lucier/692/tomography.pdf).
Kutyniok et al., ShearLab 3D: Faithful Digital Shearlet Transforms based on Compactly Supported Shearlets, (2014) (39 pages) (Cornell University Archive, arXiv No. 1402.5670v1).
R-Forge User's Manual, (2011), SVN Revision: 227, 10 pages.
Daubechies Ten Lectures of Wavelets, Springer-Verlag, (1992), from CBMS-NSF Regional Conference Series in Applied Mathematics Society for Industrial and Applied Mathematics 1990 (344 pages).
Lawton, Seven Aneurysms Tenets and Techniques for Clipping (2011) Section 1, Thieme Medical Publishers, New York, Section 1, (36 pages).
Bracewell, R. N., "Two-Dimensional Imaging", Prentice Hall, chapters 4-7, 12, and 15, 1995 (206 pages).
Des Plantes, "Eine Neue Methode Zur Differenzierung in der Rontgenographie (Planigraphies)," Acta Radiologica, 13:2, 182-192, 1932 (16 pages).
Tuy, H. K., "An Inversion Formula for Cone-Beam Reconstruction," SIAM Journal on Applied Mathematics, 43(3):546-552, 1983 (7 pages).
Wikipedia article entitled "Band-pass filter", <https://en.wikipedia.org/wiki/Band-pass_filter>, last edited on Feb. 25, 2020, accessed on Mar. 26, 2020 (4 pages).
YouTube video, "Eulerian Video Magnification" accessed online on Jun. 15, 2020 at: <https://www.youtube.com/watch?v=ONZcjs1Pjmk>, published May 23, 2012 (2 pages).
U.S. Appl. No. 62/824,582 Entitled Device and Method for Reconstructing Cardiac Frequency Phenomena in Angiographic Data, filed Mar. 27, 2019 (25 pages).
Chen, C., et al., "Optical coherence tomography based angiography [Invited]," Biomedical Optics Express, vol. 8, No. 2, p. 1056, Jan. 24, 2017 (27 pages).
Wikipedia article "Dose Area Product" accessed online on Jun. 15, 2020 at: <https://en.wikipedia.org/wiki/Dose_area_product> (2 pages).
Martin J. Murphy, "Tracking Moving Organs in Real Time", Seminars in Radiation Oncology, vol. 14, No. 1, Jan. 2004, pp. 91-100.
Frangi et al., "Multiscale Vessel Enhancement Filtering," Medical Image Computing and Computer-Assisted Intervention—MICCAI'98, Lecture Notes in Computer Science, vol. 1496, Springer Verlag, Berlin, Germany, pp. 130-137, 1998 (8 pages).
Ashmead, John, "Morlet Wavelets in Quantum Mechanics," Quanta, vol. 1, issue 1, Nov. 2012, pp. 58-70 (13 pages).
Baker et al., "Lucas-Kanade 20 Years On: A Unifying Framework," International Journal of Computer Vision 56(3), 221-255, 2004 (35 pages).
Balakrishnan et al., "VoxelMorph: A Learning Framework for Deformable Medical Image Registration," arXiv:1809.05231 [cs.CV], Sep. 1, 2019 (16 pages).
Bao et al., "Depth-Aware Video Frame Interpolation," IEEE Conference on Computer Vision and Pattern Recognition, pp. 3703-3712, 2019 (10 pages).
Butler, William E., "Wavelet brain angiography suggests arteriovenous pulse wave phase locking," Plos One, Nov. 15, 2017 (23 pages).
Chen et al., "A Labeling-Free Approach to Supervising Deep Neural Networks for Retinal Blood Vessel Segmentation," Chongqing University, China, May 1, 2017 (10 pages).
Bao et al., https://github.com/baowenbo/DAIN, "DAIN (Depth-Aware Video Frame Interpolation)", IEEE Conference on Computer Vision and Pattern Recognition, Long Beach, CVPR 2019 (9 pages).
Dalca et al., "Unsupervised Learning of Probabilistic Diffeomorphic Registration for Images and Surfaces," Jul. 23, 2019 (18 pages).
Garyfallidis et al., "Dipy, a library for the analysis of diffusion MRI data," Frontiers in Neuroinformatics, vol. 8, Feb. 21, 2014 (17 pages).
DIPY—Diffusion Imaging In Python; https://dipy.org/; accessed Mar. 1, 2021 (8 pages).
Daubechies, Ingrid, "Ten Lectures on Wavelets," CBMS-NSF Regional Conference Series in Applied Mathematics, Sep. 1992 (342 pages).
Farneback, Gunnar, "Very High Accuracy Velocity Estimation using Orientation Tensors, Parametric Motion, and Simultaneous Segmentation of the Motion Field," Proceedings Eighth IEEE International Conference on Computer Vision, Jul. 2001 (7 pages).
Felsberg and Sommer, "The monogenic signal," IEEE Transactions on Signal Processing, (49), 12, 3136-3144, 2001 (10 pages).
Chapter 2: Multiscale Vessel Enhancement Filtering, pp. 7-16, adapted from: Frangi et al., "Multiscale Vessel Enhancement Filtering," Medical Image Computing and Computer-Assisted Intervention—MICCAI'98, Lecture Notes in Computer Science, vol. 1496, Springer Verlag, Berlin, Germany, pp. 130-137, 1998 (10 pages).
Freeman and Adelson, "The Design and Use of Steerable Filters," IEEE Transactions on Pattern Analysis and Machine Intelligence, vol. 13, No. 9, pp. 891-906, Sep. 1991 (16 pages).
Gabor, D., "Theory of Communication," Sep. 24, 1945 (29 pages).
Goupillaud et al., "Cycle-Octave and Related Transforms in Seismic Signal Analysis," Geoexploration, 23, (1984/85), pp. 85-102 (18 pages).
Harris and Stephens, "A Combined Corner and Edge Detector," Alvey Vision Conference, pp. 147-151, 1988 (5 pages).
Horn and Schunck, "Determining Optical Flow," Artificial Intelligence 17, pp. 185-203, 1981 (19 pages).
Wolfram Research, "ImageDisplacements," Wolfram Language function, https://reference.wolfram.com/language/ref/ImageDisplacements.html, 2016 (5 pages).
Lucas and Kanade, "An Iterative Image Registration Technique with an Application to Stereo Vision," Proceedings DARPA Image Understanding Workshop, Apr. 1981, pp. 121-130 (10 pages).
Morlet et al., "Wave propogation and sampling theory—Part I: Complex signal and scattering in multilayered media," Geophysics, vol. 47, No. 2, Feb. 1982, pp. 203-221 (19 pages).
Shi and Tomasi, "Good Features to Track," IEEE Conference on Computer Vision and Pattern Recognition, Seattle, Jun. 1994 (8 pages).
Simoncelli and Farid, "Steerable Wedge Filters for Local Orientation Analysis," IEEE Transactions on Image Processing, 5(9): 1377-1382, 1996 (10 pages).
Unser and Van De Ville, "Wavelet Steerability and the Higher-Order Riesz Transform," IEEE Transactions on Image Processing, vol. 19, No. 3, Dec. 22, 2009 (17 pages).

(56) References Cited

OTHER PUBLICATIONS

Yin et al., "Reducing the X-ray radiation exposure frequency in cardio-angiography via deep-learning based video interpolation," Jun. 1, 2020 (6 pages).
Zhang et al., "Application of Wavelet Thresholding De-noising in DSA," International Symposium on Information Science and Engineering IEEE Computer Society, 2008, pp. 130-134.
Akram et al., "Blood Vessel Enhancement and Segmentation Using Wavelet Transform, International Conference on Digital Image Processing IEEE Computer Society," 2009, pp. 34-38.
Cao et al., "Joint Spatio-Temporal Registration and Microvasculature Segmentation of Retinal Angiogram Sequences," 33rd Annual International Conference of the IEEE EMBS, 2011, pp. 2618-2621.
Tsai et al., "Motion Estimation and Wavelet Transform in Angiogram Video Coding," IEEE, 1994, pp. 1121-1125.
Oh et al., "Reversible Wavelet Compression For Digital Angiograms," Proceedings of the 20th Annual International Conference of the IEEE Engineering in Medicine and Biology Society,1998, vol. 20, No. 3, pp. 1442-1445.
Tache et al., "Enhanced Visualization of Cerebral Blood Vessels for X-ray Angiograms," IEEE International Conference on E-Health and Bioengineering, 2013, pp. 1-13.
Sun et al., "Morphological enhancement of vascular angiogram with multiscale detected by Gabor filters," Electronics Letters, 2008, vol. 44, No. 2, pp. 1-3.
Munteanu et al., "Wavelet-Based Lossless Compression of Coronary Angiographic Images," IEEE Transactions on Medical Imaging, 1999, vol. 18, No. 3, pp. 272-281.
Lin et al., "Extraction of Coronary Arterial Tree Using Cine X-Ray Angiograms," Biomedical Engineering-Applications, Basis & Communications, 2005, pp. 111-120.
Hohne et al., "Fourier Domain Techniques for Digital Angiography of the Heart," IEEE Transactions on Medical Imaging, 1984, vol. MI-3, No. 2, pp. 62-67.
Hohne et al., "Proceedings of SPIE: Digital Angiography of The Heart in The Frequency Domain," Medical Images and Icons IEEE, 1984, pp. 245-250.
Havla et al., "Validation of a method to differentiate arterial and venous vessels in CT perfusion data using linear combinations of quantitative time-density curve characteristics," Eur. Radiol., 2015, vol. 25, pp. 2937-2944.
Farge, M., "Wavelet Transforms and Their Applications to Turbulence," Annu. Rev. Fluid Mech., 1992, vol. 24, pp. 395-457.
Havla, et al., "Classification of arterial and venous cerebral vasculature based on wavelet postprocessing of CT perfusion data," Med. Phys. (2016) 43 (2), pp. 702-709.
Medda et al., A wavelet clustering technique for the identification of functionally connected regions in the rat brain using resting state fMRI, IEEE Statistical Signal Processing Workshop (SSP), Aug. 2012, pp. 424-427.
Mizuno-Matsumoto et al., Wavelet-crosscorrelation analysis: Nonstationary analysis of neurophysiological signals, Brain Topography, 2005, vol. 17, No. 4, pp. 237-252.
Morlet et al., Wave propagation and sampling theory-part I: Complex signal and scattering in multilayered media, Geophysics, Feb. 1982, vol. 47, No. 2, pp. 203-221.
Najmi et al., The continuous wavelet transform and variable resolution time-frequency analysis, Johns Hopkins Apl Technical Digest, 1997, vol. 18, No. 1, pp. 134-140.
Schultze-Kraft et al., Exploiting the potential of three dimensional spatial wavelet analysis to explore nesting of temporal oscillations and spatial variance in simulateous EEG-fMRI data, Progress in Biophysics and Molecular Biology, Mar. 2011, vol. 105(1-2), pp. 67-79.
Serroukh, Wavelet coefficients cross-correlation analysis of times series, Electronic Journal of Applied Statistical Analysis, 2012, vol. 5, iss 2, pp. 289-296.
Shannon, Communication in the Presence of Noise, Proceedings of the IEEE, Feb. 1998, vol. 86, iss. 2, pp. 447-457.
Hardesty et al., Safety, efficacy, and cost of intraoperative indocyanine green angiography compared to intraoperative catheter angiography in cerebral aneurysm surgery, Journal of clinical neuroscience, Apr. 2014, pp. 1-6.
Hyvarinen et al., Indocyanine green fluorescence angiography, Acta Ophthalmologica, Aug. 1980, vol. 58(4), pp. 528-538.
Aaslid et al., Noninvasive transcranial doppler ultrasound recording of flow velocity in basal cerebral arteries, J Neurosurg, 1982, vol. 57(6), pp. 769-774.
Vo et al., Vonn distribution of relative phase for statistical image modeling in complex wavelet domain, Signal Processing, 2011, vol. 91(1), pp. 114-125.
Abramovich et al., Wavelet Analysis and its Statistical Applications, Journal of the Royal Statistical Society Series D (The Statistician), 2000, vol. 49(1), pp. 1-29.
Kim et al., Cine MR CSF flow study in hydrocephalus: what are the valuable parameters? Acta neurochirurgica Supplement, 1998, vol. 71(6), pp. 343-346.
Kulkarni et al., Endoscopic third ventriculostomy in the treatment of childhood hydrocephalus, The Journal of Pediatrics, Aug. 2009, vol. 155, No. 2, pp. 254-259.
Meairs et al., Ultrasound, microbubbles and the blood-brain barrier, Progress in Biophysics & Molecular Biology, Apr. 2007, vol. 93(1-3), pp. 354-362.
Saikali et al., A three-dimensional digital segmented and deformable brain atlas of the domestic pig, Journal of Neuroscience Methods, Sep. 2010, vol. 192(1), pp. 102-109.
Wilson, Monro-Kellie 2.0: The dynamic vascular and venous pathophysiological components of intracranial pressure, Journal of Cerebral Blood Flow & Metabolism, May 2016, vol. 36(8), pp. 1338-1350.
Bernstein et al., Handbook of MRI Pulse Sequences, Elsevier Academic Press, 2004, pp. 443-454.
Kim et al., Phase-shift between arterial flow and ICP pulse during infusion test, Acta Neurochirurgica, Feb. 3, 2015, vol. 157(4), pp. 633-638.
Kawoos et al., Advances in Intracranial Pressure Monitoring and its Significance in Managing Traumatic Brain Injury, International Journal of Molecular Sciences, 2015, vol. 16 (12), pp. 28979-28997.
Gabor, Theory of communication. Part 2: The analysis of hearing, Journal of the Institution of Electrical Engineers—Part III: Radio and Communication Engineering, 1946, vol. 93(26), pp. 442-445.
Goriely et al., Mechanics of the brain: perspectives, challenges, and opportunities, Biomechanics and modeling in mechanobiology, Feb. 26, 2015, vol. 14(5), pp. 931-965.
Helbok et al., Intracranial Pressure and Cerebral Perfusion Pressure Monitoring in Non-TBI Patients: Special Considerations, Neurocritical Care, 2014, vol. 21 (S2), pp. S85-S94 (published online, Sep. 11, 2014, 10 pages).
Balestreri et al., Intracranial hypertension: what additional information can be derived from ICP waveform after head injury?, Acta Neurochirurgica (wien), 2004, vol. 146(2), pp. 131-141.
Carrera et al., What Shapes Pulse Amplitude of Intracranial Pressure?, Journal of Neurotrauma, Feb. 2010, vol. 27(2), pp. 317-324.
Bangare et al., Reviewing Otsu's method for image thresholding, International Journal of Applied Engineering Research, 2015, vol. 10, No. 9, pp. 21777-21783.
Bhadelia et al., Analysis of cerebrospinal fluid flow waveforms with gated phase-contrast MR velocity measurements, American Journal of Neuroradiology, Feb. 1995, vol. 16(2), pp. 389-400.
Bonnefous et al., Quantification of arterial flow using digital subtraction angiography, Medical Physics, Oct. 2012, vol. 39, iss. 10, pp. 6264-6275.
Chang et al., Emerging techniques for evaluation of the hemodynamics of intracranial vascular pathology, The Neuroradiology Journal, Feb. 2015, vol. 28(1), pp. 19-27.
Dawkins et al., Complications of cerebral angiography: A prospective analysis of 2,924 consecutive procedures, Neuroradiology, Aug. 2007, vol. 49, iss. 9, pp. 753-759.
Torrence et al., A Practical Guide to Wavelet Analysis, Bulletin of the American Meteorological Society, Jan. 1998, vol. 79, iss. 1, pp. 61-78.

(56) References Cited

OTHER PUBLICATIONS

Zou et al., Increased Phase Synchronization between Intracranial Pressure and Arterial Blood Pressure during Elevated Intracranial Pressure in Dogs, Proceedings of the 2005 IEEE, Engineering in Medicine and Biology 27th Annual Conference, Shanghai, China, Sep. 1-4, 2005, pp. 315-318.

Unekawa et al., RBC velocities in single capillaries of mouse and rat brains are the same, despite 10-fold difference in body size, Brain Research, 2010, vol. 1320, pp. 69-73.

Grinsted et al., Application of the cross wavelet transform and wavelet coherence to geophysical time series, Nonlinear Processes in Geophysics, 2004, vol. 11, pp. 561-566.

Grist et al., Time-Resolved Angiography: Past, Present, and Future, Journal of Magnetic Resonance Imaging, 2012, vol. 36(6), pp. 1273-1286.

Jiang et al., Computational Fluid Dynamics Simulations of Intracranial Aneurysms at Varying Heart Rates: A "Patient-Specific" Study, Journal of Biomechanical Engineering, Sep. 2009, vol. 131(9), pp. 09100-1-09100-11.

Kachelriess et al., ECG-correlated image reconstruction from subsecond multi-slice spiral CT scans of the heart, Medical Physics, 2000, vol. 27(12), pp. 1881-1902.

Kirk et al., Phase-only complex-valued spatial filter, Journal of the Optical Society of America, Aug. 1971, vol. 61, iss. 8, pp. 1023-1028.

Latka et al.. Phase dynamics in cerebral autoregulation, American journal of physiology, heart and circulatory physiology, 2005, vol. 289(5), pp. H2272-H2279.

Shpilfoygel et al., X-ray videodensitometric methods for blood flow and velocity measurement: A critical review of literature, Medical Physics, Sep. 2000, vol. 27, iss. 9, pp. 2008-2023.

MistrettA, Sub-Nyquist acquisition and constrained reconstruction in time resolved angiography, Medical Physics, 2011, vol. 38, iss. 6, pp. 2975-2985.

Peng et al., Wavelet phase synchronization analysis of cerebral blood flow autoregulation, IEEE Transactions on Biomedical Engineering, Apr. 2010, vol. 57, No. 4, pp. 960-968.

Pereira et al., A DSA-based method using contrast motion estimation for the assessment of the intra-aneurysmal flow changes induced by flow-diverter stents, American Journal of Neuroradiology, Apr. 2013, vol. 34(4), pp. 808-815.

Anonymous, Artis Zeego, Data Sheet VC21, Multi-axis for interventional imaging, Oct. 2014, 36 pages, www.siemens.com/healthcare.

Babin et al., Segmentation and length measurement of the abdominal blood vessels in 3-D MRI images, Conference Proceedings IEEE Engineering in Medicine and Biology Society, Sep. 2-6, 2009, pp. 4399-4402.

Barfett et al., Intra-vascular blood velocity and volumetric flow rate calculated from dynamic 4D CT angiography using a time of flight technique, The International Journal of Cardiovascular Imaging, Oct. 2014, vol. 30(7), pp. 1383-1392.

Bhadelia et al., Cerebrospinal fluid pulsation amplitude and its quantitative relationship to cerebral blood flow pulsations: a phase-contrast MR flow imaging study, Neuroradiology, Apr. 1997, vol. 39(4), pp. 258-264.

Long et al., Spatiotemporal wavelet analysis for functional MRI, NeuroImage, Oct. 2004, vol. 23(2), pp. 500-516.

Daubechies, The wavelet transform, time-frequency localization, and signal analysis, IEEE Transactions on Information Theory, Sep. 1990, vol. 36, iss. 5, pp. 961-1005.

Gabor, Theory of communication. Part I: The analysis of information, Journal of the Institution of Electrical Engineers—Part III: Radio and Communication Engineering, Nov. 1946, vol. 93(26), pp. 429-441.

Goupillaud et al., Cycle-octave and related transforms in seismic signal analysis, Geoexploration, Oct. 1984, vol. 23, iss. 1, pp. 85-102.

Kuroiwa et al., Development and clinical application of near-infrared surgical microscope: preliminary report, Minimally invasive neurosurgery: MIN, Dec. 2001, vol. 44(4), pp. 240-242.

Markl et al., 4D Flow MRI, Journal of Magnetic Resonance Imaging (JMRI), Oct. 2012, vol. 36, iss. 5, pp. 1015-1036.

Moser et al., On the accuracy of EPI-based phase contrast velocimetry, Magnetic Resonance Imaging, Nov. 2000, vol. 18, iss. 9, pp. 1115-1123.

Nyquist et al., Certain topics in telegraph transmission theory, Transactions of the American Institute of Electrical Engineers, Feb. 1928, vol. 47, iss. 2, pp. 617-644.

Persson et al., Hydrocephalus prevalence and outcome in a population-based cohort of children born in 1989-1998, Acta Paediatrica, Jun. 2005, vol. 94, iss 6, pp. 726-732.

Provost et al., 3D Ultrafast ultrasound imaging in vivo, Physics in Medicine and Biology, Sep. 10, 2014, vol. 59, iss. 19, L1-L13.

Raabe et al., Prospective evaluation of surgical microscope-integrated intraoperative near-infrared indocyanine green videoangiography during aneuryism surgery, Journal of Neurosurgery, Dec. 2005, vol. 103, iss. 6, pp. 982-989.

Rao et al., Shear strain imaging using shear deformations, Med Phys., Feb. 2008, vol. 35(2), pp. 412-423.

Rasul et al., Is endoscopic third ventriculostomy superior to shunts in patients with non-communicating hydrocephalus? A systematic review and meta-analysis of the evidence, Acta Neurochirurgica, May 2013, vol. 155, iss 5, pp. 883-889.

Sugawara et al., Arterial path length measurements required for the pulse wave velocity, Journal of Hypertension, May 2009, vol. 27, iss. 5, pp. 1102-1104.

Tomita et al., Automated method for tracking vast numbers of FITC-labeled RBCs in microvessels of rat brain in vivo using a high-speed confocal microscope system, Microcirculation, Feb. 2008, vol. 15, iss. 2, pp. 163-174.

Unser, Sampling—50 years after Shannon, Proceedings of the IEEE, Apr. 2000, vol. 88, No. 4, pp. 569-587.

Wagshul et al., The pulsating brain: A review of experimental and clinical studies of intracranial pulsatility. Fluids and Barriers of the CNS, Jan. 18, 2011, vol. 8, iss. 5, pp. 1-23.

Weaver et al., Brain mechanical property measurement using MRE with intrinsic activation, Physics in Medicine Biology, Nov. 2012, vol. 57, No. 22, pp. 7275-7287.

Zaidi et al., Indocyanine Green Angiography in the Surgical Management of Cerebral Arteriovenous Malformations: Lessons Learned in 130 Consecutive Cases, Operative Neurosurgery, Jun. 2014, vol. 10, No. 2, pp. 246-251.

Zou et al., Intracranial pressure waves: characterization of a pulsation absorber with notch filter properties using systems analysis, J. Neurosurg Pediatrics, Jul. 2008, vol. 2(1), pp. 83-94.

Henneman et al., Phase analysis of gated myocardial perfusion single-photon emission computed tomography compared with tissue doppler imaging for the assessment of left ventricular dyssynchrony, Journal of the American College of Cardiology, Apr. 2007, vol. 49 (16), pp. 1708-1714.

Kingdom et al., Sensitivity to contrast histogram differences in synthetic wavelet-textures, Vision Research, Mar. 2001, vol. 41(5), pp. 585-598.

Li et al., Cross-frequency coupling during isoflurane anaesthesia as revealed by electroencephalographic harmonic wavelet bicoherence, Neurosciences and Neuroanaesthesia, British Journal of Anaesthesia, Mar. 2013, vol. 110(3), pp. 409-419.

Moore, A modification of the Rayleigh test for vector data, Biometrika, Apr. 1980, vol. 67(1), pp. 175-180.

Mousavi et al., A wavelet transform based method to determine depth of anesthesia to prevent awareness during general anesthesia, Computational and Mathematical Methods in Medicine, 2014, vol. 2014, pp. 1-13.

Rakhmanov et al., A cross-correlation method for burst searches with networks of misaligned gravitational-wave detectors, Institute of Physics Publishing, Classical and Quantum Gravity, Sep. 6, 2005, vol. 22(18), pp. S1311-S1320.

Wang et al., The residual phase estimation of a seismic wavelet using a renyi divergence-based criterion, Journal of Applied Geophysics, Jul. 2014, vol. 106, pp. 96-105.

Yu, Histogram Matching Seismic Wavelet Phase Estimation, May 2012, Masters thesis, University of Houston.

(56) References Cited

OTHER PUBLICATIONS

Anor et al., Modeling of blood flow in arterial trees, Focus Article, WIREs Systems Biology and Medicine, Sep.Oct. 2010, vol. 2, pp. 612-623.
Hamberg et al., Quantitative high-resolution measurement of cerebrovascular physiology with slip-ring CT, AJNR Am J Neuroradiol, Apr. 1996, vol. 17(4), pp. 639-650.
Kashif et al., Model-based non-invasive estimation of intracranial pressure from cerebral blood flow velocity and arterial pressure, Science Translational Medicine, Apr. 2012, vol. 4(129): 129ra44.
Lassen et al., Tracer Kinetic Methods in Medical Physiology, 1979, Raven Press, New York.
Linninger et al., A mathematical model of blood, cerebrospinal fluid and brain dynamics, J Mathematical Biology, Dec. 2009, vol. 59(6), pp. 729-759.
Bayer et al., Two-dimensional simulations of displacement accumulation incorporating shear strain, Ultrason Imaging, Jan. 2014, vol. 36(1), pp. 55-73.
Braun et al., High-resolution mechanical imaging of the human brain by three-dimensional multifrequency magnetic resonance elastography at 7T, NeuroImage, Apr. 2014, vol. 90, pp. 308-314.
Feingold et al., Quantitative volumetric perfusion mapping of the microvasculature using contrast ultrasound, Invest Radiol, Oct. 2010, vol. 45(10), pp. 669-674.
Gauthier et al., Assessment of quantitative perfusion parameters by dynamic contrast-enhanced sonography using a deconvolution method, an in vitro and in vivo study, J Ultrasound Med, Apr. 2012, vol. 31(4), pp. 595-608.
Johnson et al., Local mechanical properties of white matter structures in the human brain, NeuroImage, Oct. 2013, vol. 79, pp. 145-152.
Ashmead, Morelet Wavelets in quantum mechanics, Quanta, Nov. 2012, vol. 1, Issue 1, pp. 58-70.
Johnstone et al., Wavelet threshold estimators for data with correlated noise, Journal of the Royal Statistical Society: Series B (Statistical Methodology), 1997, 59(2), pp. 319-351.
Khullar et al., Wavelet-based fMRI analysis: 3-d denoising, signal separation, and validation metrics, NeuroImage, Feb. 2011, vol. 54(4), pp. 2867-2884.
Candes et al., New Tight Frames of Curvelets and Optimal Representations of Objects with C2 Singularities, Nov. 2002, pp. 1-39 (http://citeseerx.ist.psu.edu/viewdoc/download?doi=10.1.1.162.1548&rep=rep 1&type=pdf).
Cense et al., Ultrahigh-resolution high-speed retinal imaging using spectral-domain optical coherence tomography, Optics Express, May 31, 2004, vol. 12, No. 11, pp. 2435-2447 (13 pages).
Cheng et al., Mammalian DNA Methyltransferases: A Structural Perspective, Structure, Review, Mar. 2008, vol. 16, No. 3, pp. 341-350.
Coumans et al., Volumetric analysis of syringomyelia following hindbrain decompression for Chiari malformation Type I: syringomyelia resolution follows exponential kinetics, Neurosurg Focus, Sep. 2011, vol. 31, No. 3:E4, pp. 1-4.
Dahmen, Wavelet and Multiscale Methods for Operator Equations, 1997 (146 pages).
Deutsch et al., Information Flow in Entangled Quantum Systems, (1999) pp. 1-24 (https://arxiv.org/ftp/quant-ph/papers/9906/9906007.pdf).
Donoho, Compressed Sensing, Sep. 14, 2004, pp. 1-34.
Donoho et al., Message-Passing Algorithms for Compressed Sensing, PNAS, Nov. 10, 2009, vol. 106, No. 45, pp. 18914-18919.
Duverger et al., Concentrations of Putative Neurovascular Transmitters in Major Cerebral Arteries and Small Pial Vessels of Various Species, Journal of Cerebral Blood Flow and Metabolism, 1987, vol. 7, No. 4, pp. 497-501.
Eastwood, The Penrose Transform for Complex Projective Space, Cornell University Archive, Aug. 17, 2008, pp. 1-11 (https://arxiv.org/abs/0808.2321, arXiv:0808.2321v1).
Eastwood et al., Cohomology and Massless Fields, Commun. Math. Phys. (1981) vol. 78, pp. 305-351.
Edelman et al., Nitric Oxide: Linking Space and Time in the Brain, Proc. Natl. Acad. Sci. USA, Dec. 1992, vol. 89, pp. 11651-11652.
Feichtinger et al., Gabor Frames and Time-Frequency Analysis of Distributions, Journal of Functional Analysis, 1997, vol. 146, No. FU963078, pp. 464-495.
Feng et al., Conservation and Divergence of Methylation Patterning in Plants and Animals, PNAS, May 11, 2010, vol. 107, No. 19, pp. 8689-8694.
Fisher et al., Group Formation, Relatedness, and the Evolution of Multicellularity, Current Biology, Jun. 17, 2013, vol. 23, No. 12, pp. 1120-1125.
Fujimoto et al., Optical Coherence Tomography: An Emerging Technology for Biomedical Imaging and Optical Biopsy, Neoplasia, Jan.-Apr. 2000, vol. 2, Nos. 1-2, pp. 9-25.
Goriely et al., Mechanics of the brain: perspectives, challenges, and opportunities, Biomech Model Mechanobiol, 2015, vol. 14, pp. 931-965.
Guerquin-Kern et al., A Fast Wavelet-Based Reconstruction Method for Magnetic Resonance Imaging, IEEE Transactions on Medical Imaging, Institute of Electrical and Electronics Engineers, 2011, 14 pages (obtained from HAL archives-ouvertes).
Guo et al., Sparse Multidimensional Representations using Anisotropic Dilation and Shear Operators, 2005, 13 pages (https://www.math.uh.edu/~dlabate/Athens.pdf).
Han, Properties of Discrete Framelet Transforms, Math. Model. Nat. Phenom., 2013, vol. 8, No. 1, pp. 18-47 (32 pages).
Heil, What is a Frame?, Notices of the AMS, 2013, vol. 60, No. 6, pp. 748-750.
Herz et al., Ultrahigh resolution optical biopsy with endoscopic optical coherence tomography, Optics Express, Jul. 26, 2004, vol. 12, No. 15, pp. 3532-3542.
Hogeweg, Cellular Automata as a Paradigm for Ecological Modeling, Applied Mathematics and Computation, 1988, vol. 27, pp. 81-100.
Hormander, The Spectral Function of an Elliptic Operator, Acta Math, May 7, 1968, vol. 121, pp. 193-218.
Huff et al., Dnmt1-Independent CG Methylation Contributes to Nucleosome Positioning in Diverse Eukaryotes, Cell, Mar. 13, 2014, vol. 156, No. 6, pp. 1286-1297.
Januszewski et al., Flow-based evaluation of cerebral revascularization using near-infrared indocyanine green videoangiography, Neurosurg Focus, Feb. 2014, vol. 36, No. 2: E14, pp. 1-8.
Jia et al., Quantitative OCT angiography of optic nerve head blood flow, Biomedical Optics Express, Dec. 1, 2012, vol. 3, No. 12, pp. 3127-3137.
Kamble et al., A Review: Eulerian Video Motion Magnification, International Journal of Innovative Research in Computer and Communication Engineering, Mar. 2015, vol. 3, iss. 3, pp. 2384-2390.
Kim et al., Epigenetic mechanisms in mammals, Cellular and Molecular Life Sciences, 2009, vol. 66, pp. 596-612.
Kittipoom et al., Construction of Compactly Supported Sheariet Frames, Cornell University Archive, 2010, pp. 1-37 (https://arxiv.org/abs/1003.5481, arXiv:1003.5481v2).
Klimenko et al., A cross-correlation technique in wavelet domain for detection of stochastic gravitational waves, 2002, pp. 1-15 (https://arxiv.org/abs/gr-qc/0208007, arXiv:gr-qc/0208007v1).
Knopfmacher et al., Graphs, partitions and Fibonacci numbers, Discrete Applied Mathematics, 2007, vol. 155, pp. 1175-1187.
Koenig et al., Regression of Subependymal Giant Cell Astrocytoma With Rapamycin in Tuberous Sclerosis Complex, J Child Neurol., Oct. 2008, vol. 23, No. 10, pp. 1238-1239.
Kramer et al., Intraventricular fibrinolysis with tissue plasminogen activator is associated with transient cerebrospinal fluid inflammation: a randomized controlled trial, Journal of Cerebral Blood Flow & Metabolism, 2015, vol. 35, pp. 1241-1248.
Kutyniok et al., Resolution of the Wavefront Set using Continuous Sheariets, Transactions of the American Mathematical Society, May 2009, vol. 361, No. 5, pp. 2719-2754.
Kutyniok et al., Image Separation using Wavelets and Sheariets, International Conference on Curves and Surfaces, 2010, pp. 1-14 (https://www.math.tu-berlin.de/fileadmin/i26_fg-kutyniok/Kutyniok/Papers/ImageSeparation.pdf).

(56) References Cited

OTHER PUBLICATIONS

Lee, Wavelet-Vaguelette Decompositions and Homogeneous Equations, Dec. 1997, Purdue University, In Partial Fulfillment of the Requirements for the Degree of Doctor of Philosophy, 103 pages.

Lindenmayer, Developmental Algorithms for Multicellular Organisms: A Survey of L-Systems, J. Theor. Biol., 1975, vol. 54, pp. 3-22.

Lopez et al., The Cauchy problem for a forced harmonic oscillator, Revista Mexicana De Fisica, Dec. 2009, vol. 55, No. 2, pp. 196-215.

Luney et al., Acute Posterior Cranial Fossa Hemorrhage—Is Surgical Decompression Better than Expectant Medical Management?, Neurocritical Care, Apr. 12, 2016, 6 pages.

Gabor, Theory of Communication, Part 3: Frequency Compression and Expansion, 1946, vol. 93, No. 26, pp. 445-457.

Havla et al., Wavelet-based calculation of cerebral angiographic data from time-resolved CT perfusion acquisitions, Eur Radiol. Aug. 2015, vol. 25, No. 8, pp. 2354-2361 (published online Feb. 26, 2015) (8 pages).

Kamp et al., Microscope-Integrated Quantitative Analysis of Intraoperative Indocyanine Green Fluorescence Angiography for Blood Flow Assessment: First Experience in 30 Patients, Operative Neurosurgery 1, vol. 70, Mar. 2012, pp. ons65-ons74.

Mazzola et al., Pediatric Hydrocephalus: systematic literature review and evidence-based guidelines. Part 2: Management of posthemorrhagic hydrocephalus in premature infants, Nov. 2014, J Neurosurg Pediatrics (Suppl), vol. 14, pp. 8-23.

McCrory et al., Consensus statement on concussion in sport: the 4th International Conference on Concussion in Sport held in Zürich, Nov. 2012, Br J Sports Med, (2013), vol. 47, pp. 250-258.

Michod et al., Cooperation and Conflict in the Evolution of Multicellularity, 2001, The Genetics Society of Great Britain, Heredity, vol. 86, pp. 1-7.

Nehra et al., Peyronie's Disease: AUA Guideline, American Urological Association (AUA) Guideline, approved Apr. 2015, pp. 1-41.

Forbes et al., Statistical Distributions, Fourth Edition, copyright 2011, John Wiley and Sons, Inc., Chapters 1-9, (84 pages).

Mandelshtam et al., Harmonic inversion of time signals and its applications, AIP The Journal of Chemical Physics 1997, vol. 107, No. 6756, 12 pages.

Schroeder, The Simple Harmonic Oscillator, copyright 2015-2016, 5 pages (https://physics.weber.edu/schroeder/quantum/Harmonic.pdf).

International Standards Organization, ISO/IEC 14496-12 Multimedia Formats Information Technology—Coding of audio-visual objects (2008) 4 pages (Abstract).

Guido et al., Introduction to the special issue on wavelet-based algorithms for medical problems (2007) vol. 37, p. 429.

Abdallah, Considerations in perioperative assessment of valproic acid coagulopathy, review article, Journal of Anaesthesiology Clinical Pharmacology, Jan.-Mar. 2014, vol. 30, iss. 1, pp. 7-9.

D'Agnolo et al., Radon-Penrose transform for D-modules, Sep. 6, 1994, pp. 1-37.

Penkov, A Geometric Approach to the Linear Penrose Transform, Transactions of the American Mathematical Society, Aug. 1985, vol. 290, No. 2, pp. 555-575.

Wolfram, Statistical mechanics of cellular automata, The American Physical Society, Reviews of Modern Physics, vol. 55, No. 3, Jul. 1983, pp. 601-644.

Sturm et al., New Brain Tumor Entities Emerge from Molecular Classification of CNS-PNETs, Cell, Feb. 25, 2016, vol. 164, iss. 5, pp. 1060-1072.

Liebling et al., Wavelet-based Synchronization of Nongated Confocal Microscopy Data for 4D Imaging of the Embryonic Heart, Proceedings of SPIE 5914, Wavelets XI, 2005, vol. 591409, 6 pages.

Ehrenreich et al., New developments in the understanding of cerebral vasoregulation and vasospasm: the endothelin-nitric oxide network, CME Credit, Cleveland Clinic Journal of Medicine, Mar.-Apr. 1995, vol. 62, No. 2, pp. 105-116.

Vagharshakyan et al., Light Field Reconstruction Using Shearlet Transform, Sep. 29, 2015, pp. 1-12 (Cornell University Archive, https://arxiv.org/abs/1509.08969, arXiv:1509.08969v1).

Daubechies, Orthonormal Bases of Compactly Supported Wavelets, Communications on Pure and Applied Mathematics, 1988, vol. XLI, pp. 909-996.

Mandelshtam, The Multidimensional Filter Diagonalization Method, Journal of Magnetic Resonance, 2000, vol. 144, pp. 343-356.

Insolera et al., Cortical neurogenesis in the absence of centrioles, Nat Neurosci, Nov. 2014, vol. 17, No. 11, pp. 1528-1536.

Kool et al., Molecular subgroups of medulloblastoma: an international meta-analysis of transcriptome, genetic aberrations, and clinical data of WNT, SHH, Group 3, and Group 4 medulloblastomas, 2012, Acta Neuropathol, vol. 123, pp. 473-484.

Kutyniok et al., Compactly Supported Shearlets, Approximation Theory XIII: San Antonio 2010, pp. 1-24.

Liner, An overview of wavelet transform concepts and applications, University of Houston, Feb. 26, 2010, pp. 1-17.

Liu et al., Motion Magnification, ACM Transactions on Graphics (TOG), Jul. 2005, vol. 24, iss. 3, pp. 519-526 (8 pages).

Lohani et al., Intrasacral meningocele in the pediatric population, J Neurosurg Pediatrics, Jun. 2013, vol. 11, pp. 615-622.

Long et al., Spatiotemporal wavelet analysis for functional MRI, NeuroImage, 2004, vol. 23, pp. 500-516.

Maltz et al., Fixed gantry tomosynthesis system for radiation therapy image guidance based on a multiple source x-ray tube with carbon nanotube cathodes, Medical Physics, May 2009, vol. 36, No. 5, pp. 1624-1636.

Mandelshtam, FDM: the filter diagonalization method for data processing in NMR experiments, Progress in Nuclear Magnetic Resonance Spectroscopy, 2001, vol. 38, pp. 159-196.

Mourant et al., Hemoglobin parameters from diffuse reflectance data, Journal of Biomedical Optics, Mar. 2014, vol. 19, No. 3, pp. 037004-1-037004-9.

D'Ariano, How to Derive the Hilbert-Space Formulation of Quantum Mechanics From Purely Operational Axioms, 20 pages (presented at conference "On the Present Status of Quantum Mechanics" held on Sep. 7-9, 2005, Mali Losinj, Croatia) (Cornell University Archive, https://arxiv.org/abs/quant-ph/0603011, arXiv:quant-ph/0603011v1).

Mixter, Ventriculoscopy and Puncture of the Floor of the Third Ventricle, Boston M. & S. Journal, Mar. 1, 1923, vol. 188, No. 9, p. 277-278.

Moussa et al., Efficacy of postoperative antibiotic injection in and around ventriculoperitoneal shunt in reduction of shunt infection: A randomized controlled trial, Clinical Neurology and Neurosurgery, 2016, vol. 143, pp. 144-149.

Monici, Cell and tissue autofluorescence research and diagnostic applications, Biotechnology Annual Review, 2005, vol. 11, pp. 227-256.

Drexler et al., In vivo ultrahigh-resolution optical coherence tomography, Optics Letters, Sep. 1, 1999, vol. 24, No. 17, pp. 1221-1223.

Rees et al., Role of endothelium-derived nitric oxide in the regulation of blood pressure, Proc. Natl. Acad. Sci. USA, 1989, vol. 86, pp. 3375-3378.

Rodino et al., The Gabor Wave Front Set (2013) (Cornell University Archive, https://arxiv.org/abs/1207.5628, arXiv:1207.5628v2), pp. 1-29.

Schaer et al., Haptoglobin Preserves Vascular Nitric Oxide Signaling during Hemolysis, American Journal of Respiratory and Critical Care Medicine, May 15, 2016, vol. 193, iss. 10, pp. 1111-1122.

Shumacher, Analog clock and watch reader, 2015, pp. 1-10 (https://www.cs.bgu.ac.il/~ben-shahar/Teaching/Computational-Vision/StudentProjects/ICBV151/ICBV-2015-1-ChemiShumacher/Report.pdf).

Tudor et al., Endoscopic third ventriculostomy (ETV) for idiopathic normal pressure hydrocephalus (iNPH) (Review), Cochran Collection, Cochrane Database of Systematic Reviews, 2015, iss. 7, pp. 1-23.

Khandelwal et al., Age-dependent increase in green autofluorescence of blood erythrocytes, J. Biosci. Sep. 2007, vol. 32, No. 6, pp. 1139-1145.

(56) References Cited

OTHER PUBLICATIONS

Wadhwa et al., Phase-Based Video Motion Processing, MIT Computer Science and Artificial Intelligence Lab, ACM Transactions on Graphics, Jul. 2013, vol. 32, No. 4, article 80, p. 80:1-80:9.

Yang et al., Improved phase-resolved optical Doppler tomography using the Kasai velocity estimator and histogram segmentation, Optics Communications, Jul. 15, 2002, vol. 208, pp. 209-214.

Zhang et al., Orthogonal Complex Filter Banks and Wavelets: Some Properties and Design, IEEE Transactions on Signal Processing, Apr. 1999, vol. 47, No. 4, pp. 1039-1048.

Aaslid et al., Cerebral Autoregulation Dynamics in Humans, Stroke, 1989, vol. 20, pp. 45-52.

Adams et al., Symptomatic Occult Hydrocephalus with "Normal" Cerebrospinal-Fluid Pressure, A Treatable Syndrome, The New England Journal of Medicine, Jul. 15, 1965, vol. 273, No. 3, pp. 117-126.

Barina, Gabor Wavelets in Image Processing, Feb. 10, 2016, 6 pages (Cornell University Archive, https://arxiv.org/pdf/1602.03308.pdf, arXiv:1602.03308v1).

Bernardes et al., Digital Ocular Fundus Imaging: A Review, Ophthalmologica, 2011, vol. 226, pp. 161-181.

Bernardino et al., A Real-Time Gabor Primal Sketch for Visual Attention, Second Iberian Conference on Pattern Recognition and Image Analysis, 2005, 8 pages (http://vislab.isr.ist.utl.pt/publications/05-ibpria-alex.pdf).

Guo et al., Wavelets with composite dilations and their MRA properties, Applied and Computational Harmonic Analysis, 2006, vol. 20, pp. 202-236.

Goh et al., Subependymal giant cell tumors in tuberous sclerosis complex, Neurology, Oct. 2004, vol. 63, pp. 1457-1461.

Bo et al., Symbolic Representations in Motor Sequence Learning, Neuroimage, 2011, vol. 54, No. 1, pp. 417-426.

Bodranghien et al., Consensus Paper: Revisiting the Symptoms and Signs of Cerebellar Syndrome, Cerebellum, Jun. 2016, vol. 15, No. 3, pp. 369-391 (published online Jun. 2015) (23 pages).

Borsdorf et al., Separate CT-Reconstructions for 3D Wavelet Based Noise Reduction Using Correlation Analysis, 2007, IEEE Nuclear Science Symposium Conference Record, pp. 2633-2638.

Brouder et al., A Smooth Introduction to the Wavefront Set, Apr. 7, 2014, pp. 1-29 (Cornell University Archive, https://arxiv.org/pdf/1404.1778.pdf, arXiv:1404.1778v1).

Burt et al., The Laplacian Pyramid as a Compact Image Code, IEEE Transactions on Communications, Apr. 1983, vol. COM-31, No. 4, pp. 532-540.

Wendy Bottinor, MD, et al. "Adverse Reactions to Iodinated Contrast Media", International Journal of Angiology, vol. 22, No. 3/2013, Aug. 16, 2013, 5 pages.

Yumi Yanaga, et al., "Contrast Material Injection Protocol With the Dose Adjusted to the Body Surface Area for MDCT Aortography", AJR:194, Apr. 2010, 6 pages.

Keika Ose, et al., "'Gadolinium' as an Alternative to Iodinated Contrast Media for X-Ray Angiography in Patients With Severe Allergy", Circ J 2005; 69: 507-509, Circulation Journal, vol. 69, Apr. 2005, 3 pages.

H. Kälsch, M.D., et al., "Gadolinium-Based Coronary Angiography in Patients with Contraindication for Iodinated X-Ray Contrast Medium: A Word of Caution", Journal of Interventional Cardiology, vol. 21, No. 2, 2008, 9 pages.

Rohit S. Loomba, MD, et al., "Comparison of Contrast Volume, Radiation Dose, Fluoroscopy Time, and Procedure Time in Previously Published Studies of Rotational Versus Conventional Coronary Angiography", The American Journal of Cardiology, Am J Cardiol 2015; 116:43e49, 7 pages.

Hrvoje Lusic, et al., "X-Ray Computed Tomography Contrast Agents", Chem Rev. Mar. 13, 2013; 113(3), NIH-PA Author Manuscript, 64 pages.

Kreton Mavromatis, MD, "The Imperative of Reducing Contrast Dose in Percutaneous Coronary Intervention", Editorial Comment, JACC: Cardiovascular Interventions, vol. 7, No. 11, 2014, 3 pages.

Sun Y. Lee, et al., "A Review: Radiographic Iodinated Contrast Media-Induced Thyroid Dysfunction", J Clin Endocrinol Metab., Feb. 2015; 100(2): 376-383, Published online Nov. 6, 2014, 15 pages.

Romain Lacroix, "3D Optical flow analysis of a pulsed contrast agent in the bloodstream. Application to virtual angiography and Magnetic Particle Imaging", Medical Imaging, Télécom Bretagne; Université de Bretagne Occidentale, Apr. 5, 2016, English, tel-01298049, https://hal.archives-ouvertes.fr/tel-01298049/document, 48 pages.

Jerome Revaud, et al., "EpicFlow: Edge-Preserving Interpolation of Correspondences for Optical Flow", May 19, 2015, https://arxiv.org/pdf/1501.02565v2.pdf, 11 pages.

Navid Nourani-Vatani, et al., "A Study of Feature Extraction Algorithms for Optical Flow Tracking", Dec. 5, 2012, https://www.araa.asn.au/acra/acra2012/papers/pap105.pdf, 7 pages.

Kritika Iyer, et al., "AngioNet: a convolutional neural network for vessel segmentation in X-ray angiography", Scientific Reports, www.nature.com/scientificreports/, (2021) 11:18066, https://doi.org/10.1038/s41598-021-97355-8, 13 pages.

Notification of Reasons for Refusal with English translation, in Japanese Patent Application No. 2021-541303, dated Sep. 9, 2022, 10 pages.

Examination Report in Great Britain Patent Application No. GB2110188.6, dated Aug. 30, 2022, 3 pages.

Examination Report in Canadian Patent Application No. 3,126,986, dated Sep. 21, 2022, 4 pages.

* cited by examiner

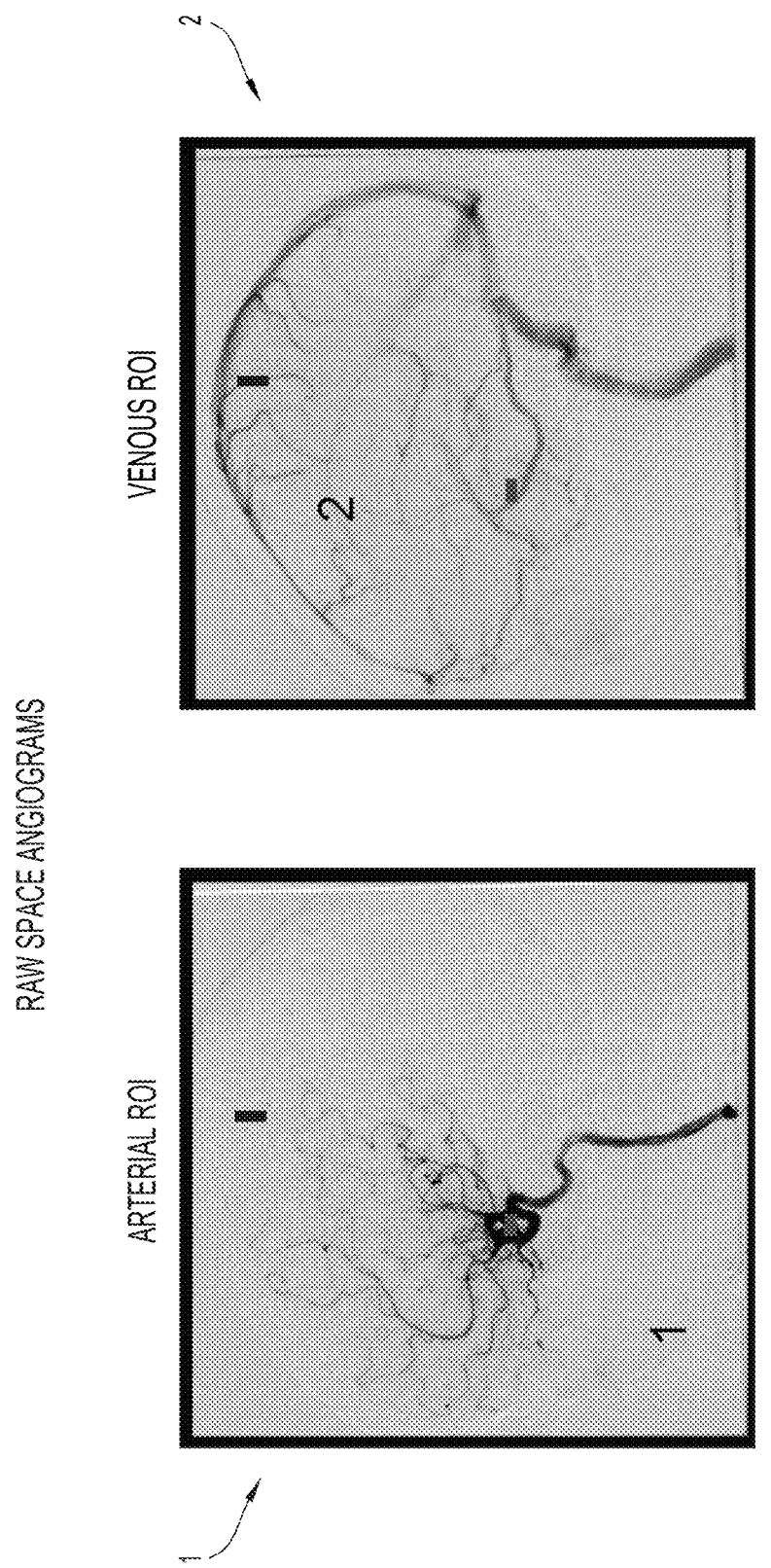

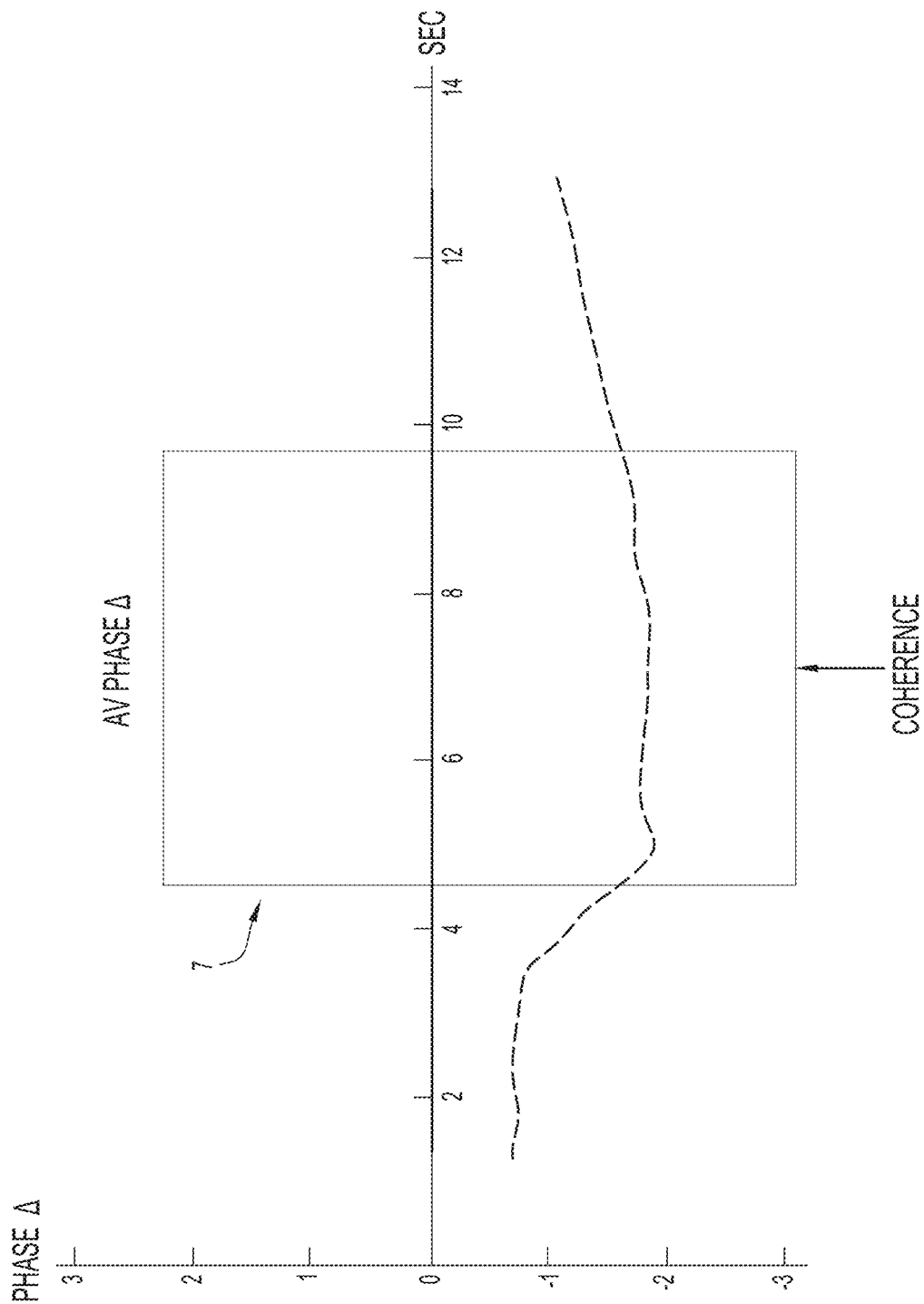

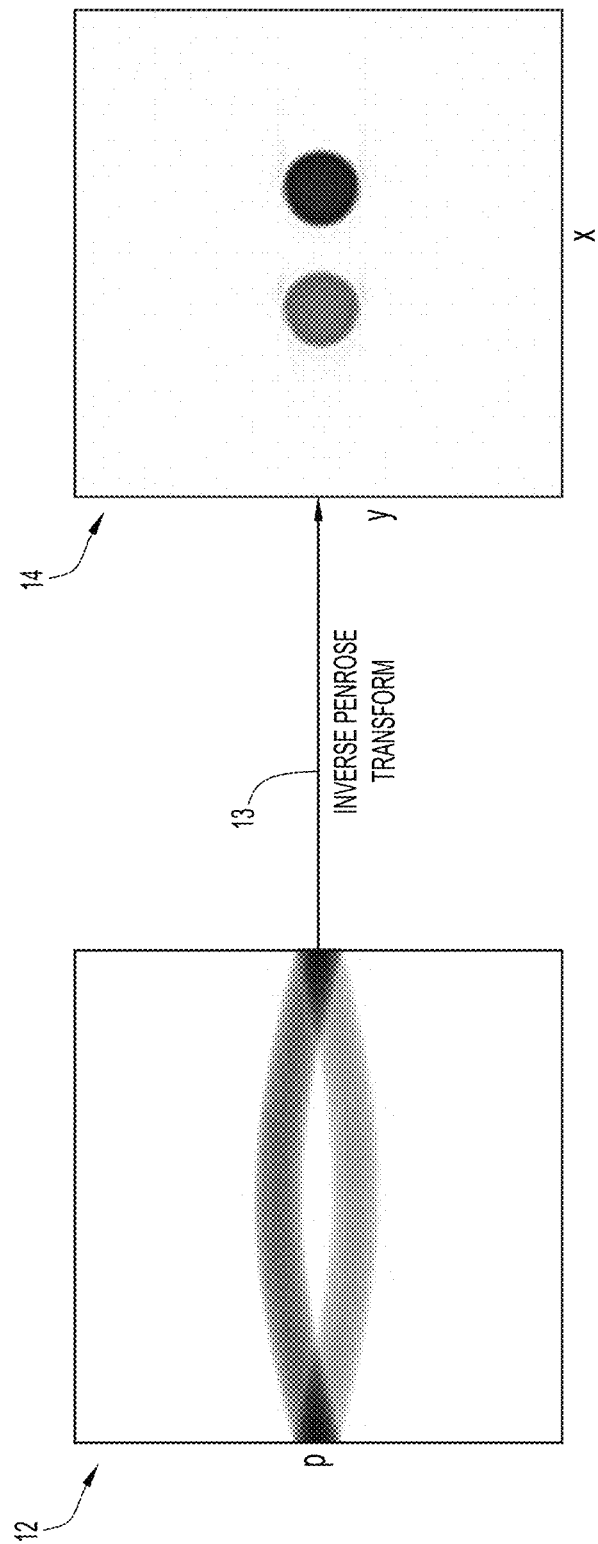

SPATIOTEMPORAL RECONSTRUCTION IN HIGHER DIMENSIONS OF A MOVING VASCULAR PULSE WAVE FROM A PLURALITY OF LOWER DIMENSIONAL ANGIOGRAPHIC PROJECTIONS

CROSS REFERENCE TO RELATED APPLICATIONS

This application claims the benefit of and priority under 35 U.S.C. § 119 to Provisional Patent Application No. 62/801,766, filed Feb. 6, 2019, which is also incorporated in its entirety into the present application by reference.

FIELD OF THE INVENTION

Techniques for creating a higher order dimensional reconstruction of a moving vascular pulse wave from a plurality of lower order dimensional angiographic projections are provided. Since an angiogram (e.g., x-ray angiogram) is commonly produced as a two-dimensional cine projection of angiographic contrast traveling as a function of time in a 3D vascular bed, this method includes reconstruction of the angiogram in four dimensions, including a 3D space and a time dimension, based on cardiac frequency angiographic phenomena.

Present techniques reconstruct an angiogram into three spatial dimensions from multiple angiographic image projections, each image projection obtained in two spatial dimensions. These techniques may be applied to obtain higher order dimensional spatiotemporal reconstructions from lower order spatial dimensions using vascular pulse waves and other cardiac frequency phenomena.

According to present techniques, the lower order dimensional angiographic projections may be acquired simultaneously, in series, or in some combination thereof.

According to present techniques, the physiological coherence at cardiac frequency is employed to synchronize each two spatial dimensional image projection. Synchronization based on physiological coherence allows reconstruction due to the temporal consistency of cardiac frequency angiographic phenomena as synchronized to a single cardiac frequency pacemaker or other external source.

Present methods, devices, and computer-readable media utilize the physiological coherence of vascular pulse waves to permit tomosynthesis of a 3D spatial reconstruction of a vascular pulse wave from two spatial dimensional image projections.

BACKGROUND

The heart pumps blood throughout the vascular system, including to organs, as a sequence of arterial stroke volumes. The method of cardiac gating does not allow the imaging of individual stroke volumes while traveling though vessels but instead interpolates a pulse wave from many heartbeats. U.S. Pat. No. 10,123,761 discloses aspects of performing spatiotemporal reconstruction of individual moving vascular pulse waves from angiographic images acquired at faster than cardiac frequency. In this approach, the moving vascular pulse wave is reconstructed into a two spatial dimensional angiographic projection. In aspects, a balance of motion alias and frequency alias techniques are employed. However, this approach is limited by the inability to offer spatiotemporal reconstruction of a moving vascular pulse wave in three spatial dimensions.

U.S. Pat. No. 10,123,671 discloses techniques for analyzing a sequence of angiographic images acquired at faster than cardiac rate to obtain a spatiotemporal reconstruction of moving vascular pulse waves according to that image projection. The spatiotemporal reconstructions are complex valued data of the same dimensionality as the projection. Each pixel at each time point has a complex valued datum. It may be represented as a real number and an imaginary number. For physiological interpretation, however, it is represented in polar form with a magnitude and a phase. The magnitude represents the variation of contrast in that pixel at cardiac frequency. The phase represents the position in the cardiac cycle.

Computational approaches to higher dimensionality reconstruction from lower dimensionality projections may use techniques such as inversion of a generalized Radon transform, filtered back projection, constrained inversion, iterative techniques, expectation-maximization, and other algorithms. These methods assume that the object being imaged does not vary between one projection angle and the next. Accordingly, these approaches are suitable for real valued projection data, for example, to describe the attenuation of x-rays by the object being imaged by projections.

However, these methods are not suitable for reconstruction of dynamic phenomenon because the subject of the reconstruction, which is visualized using a contrast agent, varies between projections.

Other techniques are known in the art that involve reconstruction of higher dimensional images from multiple data sets of lesser dimensionality. However, these techniques also apply to reconstruction of static anatomical x-ray images, obtained from a plurality of image projections. However, dynamic information, such as vascular pulse waves and other cardiac frequency phenomena, would not be obtained from processing of static images.

OBJECTS OF THE INVENTION

U.S. Pat. No. 10,123,761, which is incorporated herein by reference in its entirety, discloses spatiotemporal reconstruction of vascular pulse waves by wavelet techniques within a two spatial dimensional angiographic projection. Two dimensional vascular pulse waves (included in cardiac frequency angiographic phenomena), which are dynamic, transient, and periodically reoccurring, may be used in the reconstruction of higher spatial dimensional images of vascular pulse waves. Spatially distributed vascular pulse waves are physiologically coherent at cardiac frequency in normal human tissues, organs, and vasculature, particularly including the brain. "Physiological coherence at cardiac frequency" is defined to be when different spatial regions of a vascular bed maintain a relatively fixed phase difference over a plurality of cardiac cycles.

An object of the invention is to provide spatiotemporal reconstruction of vascular pulse waves in three spatial dimensions from two dimensional image projections, by utilizing the presence of vascular pulse waves in two dimensions.

As used herein, "spatiotemporal reconstruction" is defined to be a reconstruction of a higher order dimensionality object from a plurality of image projections of a lower order dimensionality. For example, generation of a two spatial dimensional image of an object from a plurality of sequences of one spatial dimensional image projections, represents a spatiotemporal reconstruction. As another example, generation of a three spatial dimensional representation of an object from a plurality of sequences of two spatial dimensional image projections, represents a spatiotemporal reconstruction. The image projections may be obtained by any suitable angiographic imaging technique, including but not limited to, parallel beam geometry, fan beam geometry, cone beam geometry, or other methods.

Spatiotemporal reconstruction of a higher order dimensionality object from a lower order dimensionality object may utilize any suitable computational technique, including but not limited to inverse Penrose transform techniques, or any other suitable transform capable of operating on complex-valued data. These techniques offer an approach for reconstructing higher order spatial dimensionality images from lower order spatial dimensional angiographic image projections, in cases in which the spatial distribution of the angiographic contrast used to visualize blood flow varies systematically between image projections.

Moving vascular pulse waves are suitably described with complex valued data. Every pixel being reconstructed can be represented as having a real and imaginary component, and may be visualized based on cardiac frequency magnitude and phase. Therefore, spatiotemporal reconstruction may be performed with techniques that can operate on complex valued image projection data. For example, the complex valued version of the inverse Radon transform, the inverse Penrose transform, may be used for such reconstructions. Although the examples provided herein utilize the inverse Penrose transform as the computational arm of the reconstruction of a complex-valued higher order spatial dimensional angiographic image from complex-valued projections of lower order spatial dimensionality, it should be understood that these techniques may apply to any suitable algorithm for performing spatiotemporal reconstruction using complex-valued projection data.

SUMMARY OF THE INVENTION

In order to overcome the inability to perform higher order dimensional spatiotemporal reconstruction from lower order dimensional projections because of the ongoing variation in angiographic contrast between projections, present techniques utilize physiological coherence of vascular pulse waves and algorithms designed for processing complex-valued projections.

In an embodiment, a plurality of lower order angiographic projections is obtained from a transiting or transient bolus of angiographic contrast administered to a subject. Projections may be obtained by a combination of multiple simultaneous projection devices, each comprising an x-ray source diametrically oriented to an x-ray sensor, by rapid motion of projection devices about the imaged object, or by projections obtained from separate angiographic bolus travels.

Methods, systems, devices, and computer program products are provided herein for reconstructing a higher dimensional cine representation of spatiotemporal cardiac frequency phenomena from a plurality of lower dimensional synchronized projections of reconstructed spatiotemporal cardiac frequency phenomena, the reconstruction performed using physiological coherence at cardiac frequency in the spatiotemporal reconstructions of angiographic phenomena and complex valued methods for operating on the projections.

Methods, systems, devices, and computer program products are provided herein for reconstructing a higher dimensional spatial representation of spatiotemporal cardiac frequency phenomena from a plurality of lower dimensional image projections, obtained using angiography, comprising: obtaining a plurality of sequences of image projections of an object at faster than cardiac frequency; processing each of the plurality of sequences independently to obtain a plurality of sequences corresponding to cardiac frequency angiographic phenomena; synchronizing the plurality of sequences corresponding to cardiac frequency angiographic phenomena using physiological coherence; and processing the synchronized plurality of sequences with complex valued methods to generate a higher level spatial reconstruction of the cardiac frequency angiographic phenomena.

In aspects, the plurality of sequences are obtained with reference to an index source.

In aspects, the index source is obtained from a physiological marker, a pulse oximeter, an electrocardiogram, or an intracranial pressure waveform.

In aspects, a 3D reconstruction is generated from a plurality of 2D image projections, or a 2D reconstruction is generated from a plurality of 1D image projections.

Methods, systems, devices, and computer program products are provided herein for synchronizing moving vascular pulse waves in each of separate projections, the method comprising using angiographic coherence at cardiac frequency to synchronize separate projections of reconstructed spatiotemporal cardiac frequency phenomena.

Methods, systems, devices, and computer program products are provided herein for reconstructing a higher dimensional representation of cardiac frequency angiographic phenomena from biplane data, comprising: obtaining angiographic data, wherein the angiographic data comprises two sequences of 2D image projections of a 3D object obtained at the same point in time, wherein the sequences are obtained at faster than cardiac frequency; processing each sequence independently to obtain spatiotemporal cardiac frequency phenomena; position, on a frame-by-frame basis, the first projection and the second projection orthogonal to each other in a volumetric space, and project the first projection along a first axis and the second projection along a second axis; for voxels that intersect, filtering the voxels such that voxels having a coherence value greater than a threshold are retained; generating a 3D reconstruction of the spatiotemporal cardiac frequency phenomena based on the filtered voxels.

In aspects, the first sequence is shifted to align the first sequence with the second sequence relative to an SI dimension.

In aspects, filtering further comprises discarding voxels having a coherence value less than a threshold.

In aspects, the first or/and second sequence of image projections is transposed in order to align the first and second sequences in a 3D space.

In aspects, the coherence value is set at a threshold indicating that the intersecting voxels correspond to the same vessel.

If a high speed tomographic system obtains image projections sufficiently fast for reconstructed images to be produced at faster than cardiac rate, the spatiotemporal reconstruction techniques for moving vascular pulse waves as disclosed by U.S. Pat. No. 10,123,761 may be applied.

According to the present techniques, the physiological coherence of the vascular bed is utilized to express the phase of every pixel with respect to an index source, in a process referred to as phase indexing. The index source may be a specific structure within the angiographic image, so long as it is present in all projections. This may include, for example, a named artery or a named vein. The index source for phase indexing may be a reference cardiac signal selected independently from the images, for example, a pulse oximeter, an electro cardiogram, or an intracranial pressure waveform.

In an embodiment, phase indexing is performed using complex-valued arithmetic between the reference cardiac signal and every pixel at every time point of every projection.

Thus, for every image projection, a complex valued representation of contrast variation referenced to a reference cardiac signal, including vascular pulse wave activity is obtained. The plurality of image projections are reconstructed into a single higher order dimensionality representation using a complex-valued computational technique, such as an inverse Penrose transform, optionally with filtering.

BRIEF DESCRIPTION OF THE DRAWINGS

For a more complete understanding of the techniques provided herein, reference is made to the following description and accompanying drawings.

FIGS. 1A-1F illustrate angiographic physiological coherence, shown in two dimensions, based on angiographic data obtained in the human brain, according to aspects of the present embodiments. FIG. 1A shows an arterial region of interest. FIG. 1B shows a venous region of interest. FIG. 1C shows a time signal curve of the arterial and venous flow.

FIG. 1D shows a frame of a cardiac frequency space angiogram, wherein the angiogram data from FIGS. 1A and 1B have been mathematically transformed to illustrate cardiac frequency angiographic phenomena. FIGS. 1E and 1F show magnitude and phase graphs of the cardiac frequency angiographic phenomena.

FIGS. 3A-3B illustrate the inverse Penrose transform of a complex-valued sinogram as shown at FIG. 3A, made from projections of FIG. 2. The reconstructed object is shown at FIG. 3B, according to aspects of the present embodiments.

FIG. 4A shows an illustration of combining various angiograms to obtain a higher order dimensional reconstruction, according to aspects of the present embodiments. FIG. 4B shows a flow diagram of the operations of FIG. 4A, according to aspects of the present embodiments.

FIG. 8A shows a rotational x-ray system with a gantry having a C-arm according to aspects of the present embodiments. FIG. 8B shows a rotational x-ray system with a gantry and components for controlling the gantry, according to aspects of the present embodiments. FIG. 8C shows another embodiment of an x-ray system configured for biplane image acquisition, according to aspects of the present embodiments.

DETAILED DESCRIPTION

Angiographic cardiovascular phenomena may be visualized by processing angiographic data obtained at faster than cardiac frequency, e.g., twice the Nyqvist rate or greater. This phenomena, including physiological coherence, is dynamic, transient, and periodically reoccurring, and may be visualized as vascular pulse waves. Physiological coherence occurs when different spatial regions of a vascular bed maintain a relatively fixed phase difference over a plurality of cardiac cycles. As described herein, angiographic cardiovascular phenomena may be used to reconstruct higher order spatial dimensional objects and visualize vascular pulse waves from lower order image projections.

The following examples illustrate angiographic physiological coherence with human vascular brain data. However, angiographic physiological coherence is not intended to be limited to this example, and may be found in a variety of other organs with vascular components or other systems with suitable vasculature. Further, the techniques provided herein are not intended to be limited to lower dimensionality data, as found in the example embodiments.

Figure 1C:
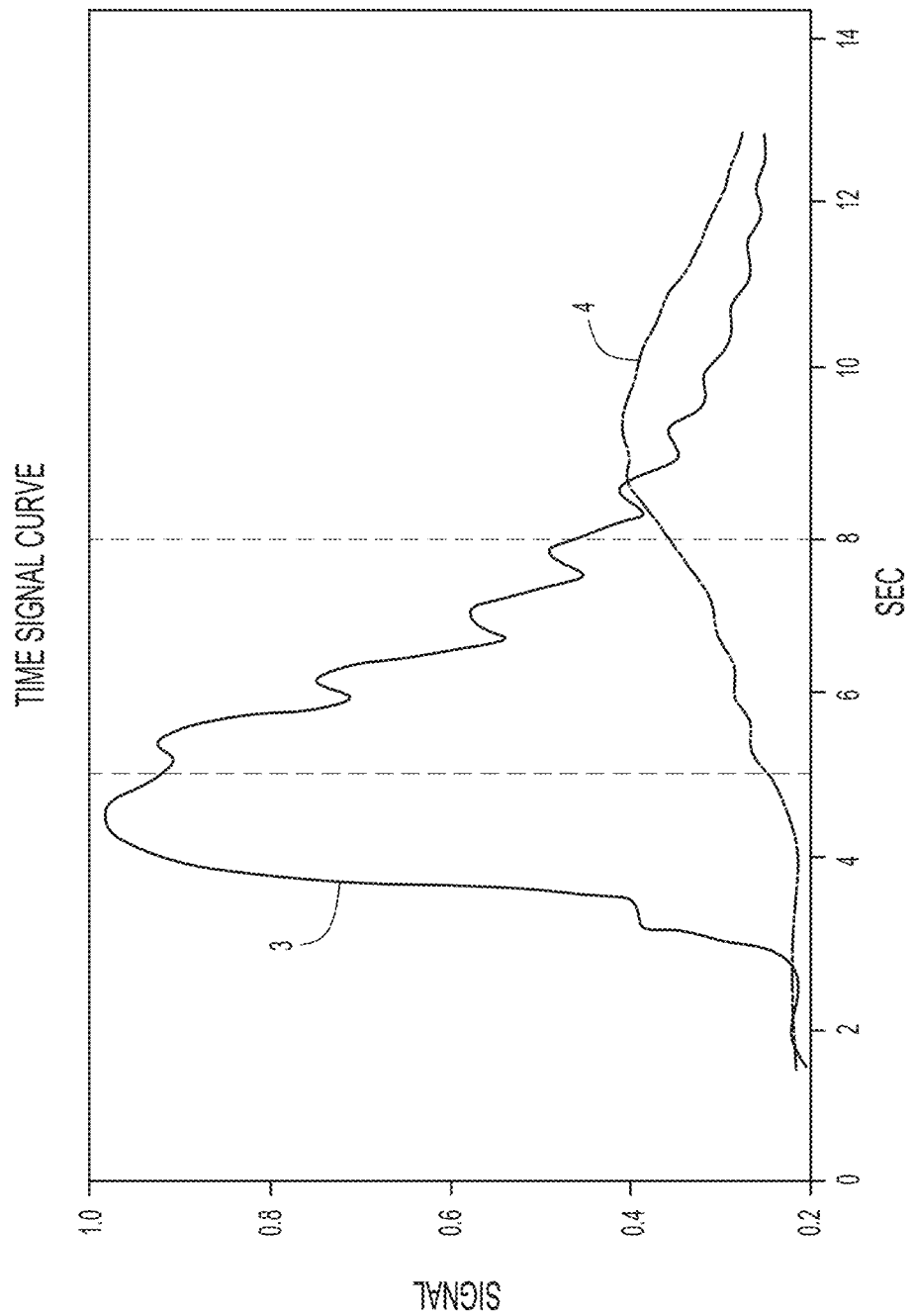
Figure 1D:
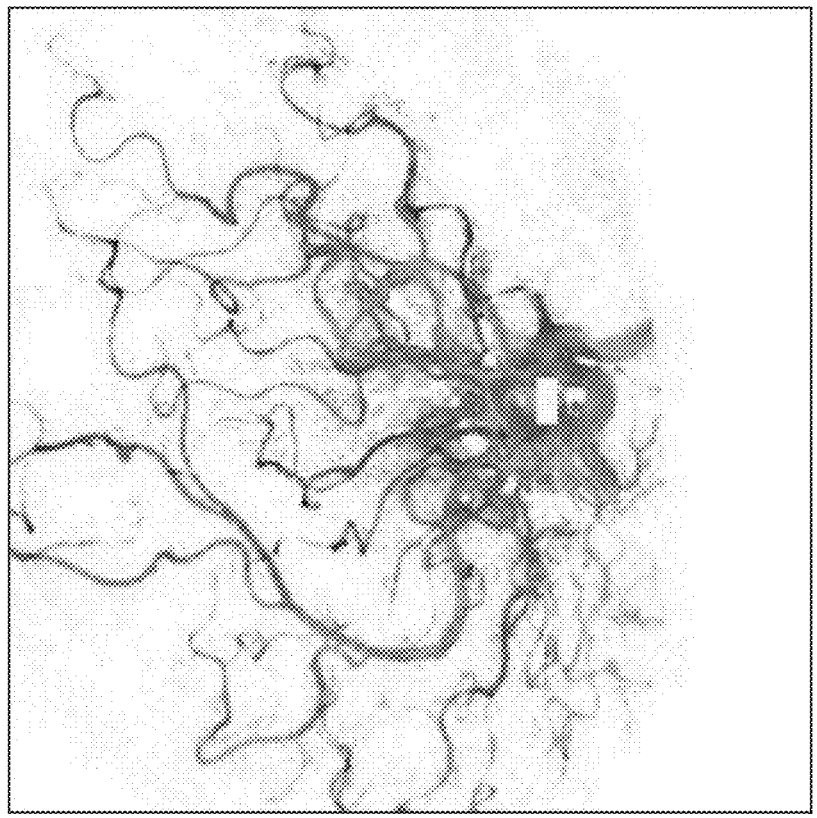
Figure 1E:
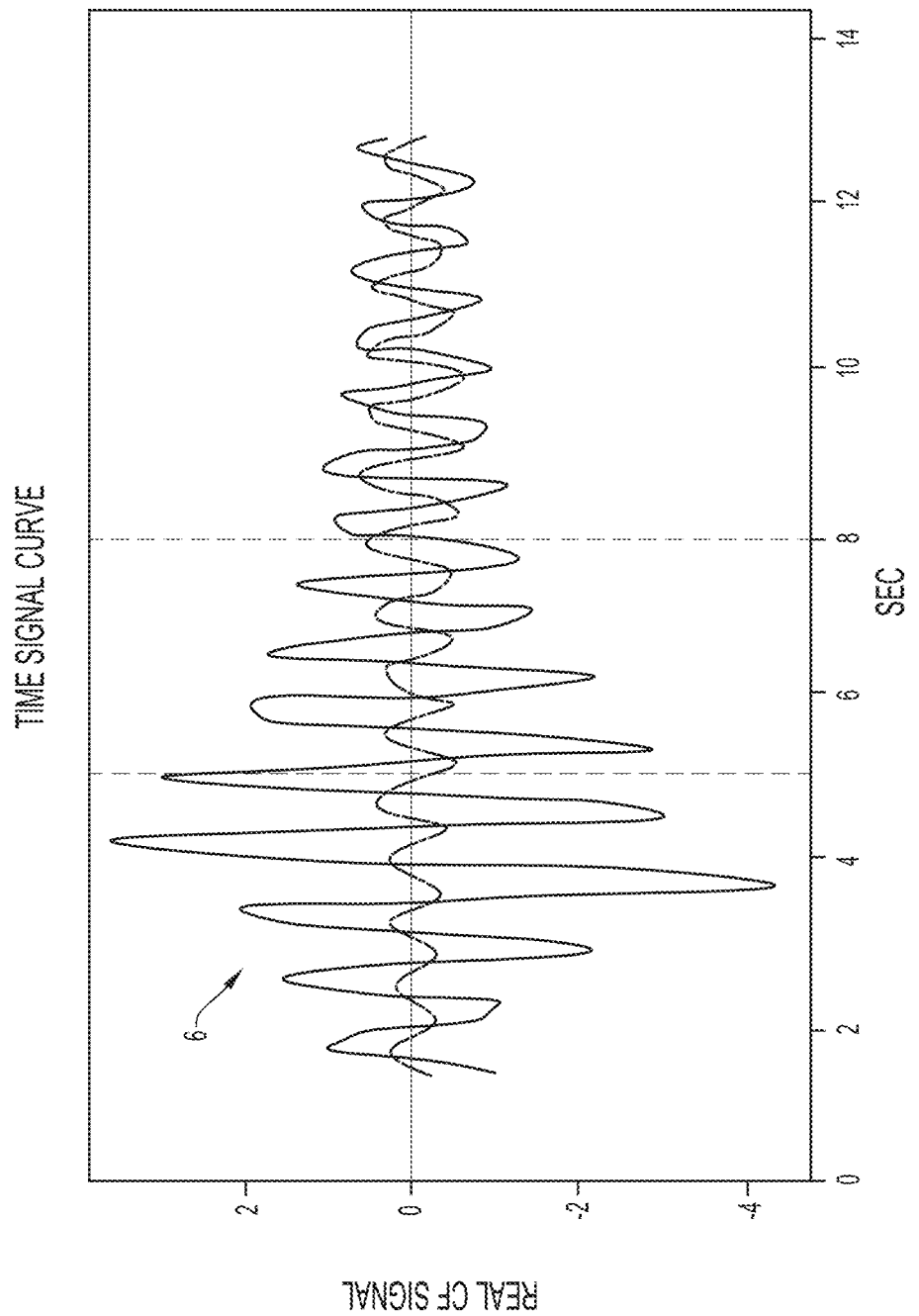

FIGS. 1A-1F show an example of angiographic physiological coherence in a human organ, in this case, the brain. FIG. 1A shows an arterial region of interest (ROI) 1 and FIG. 1B shows a venous ROI 2. The temporal profile of the passage of the angiographic contrast bolus through the arterial ROI generates an arterial time signal curve 3 as shown in FIG. 1C. Likewise, the temporal profile of the passage of the angiographic contrast bolus through the venous ROI generates a venous time signal curve 4, also shown in FIG. 1C. The angiographic projections are reconstructed into a complex-valued rendering of moving vascular pulse waves, with an example angiographic frame labeled as cardiac space angiogram 5 as shown in FIG. 1D. The temporal profile of activity in the two ROIs (e.g., arterial and venous) in cardiac space angiogram 5 shows oscillation of the signal in the arterial region of interest (ROI) 1 and in the venous ROI 2 as shown in FIG. 1E. Since these temporal profiles are obtained from the cardiac space angiogram, these profiles oscillate at cardiac frequency. The maintenance of a consistent cardiac frequency phase difference between pulse waves in the arterial ROI and the venous ROI indicates coherence between the arterial and venous ROIs as shown in FIG. 1F.

Figure 2:
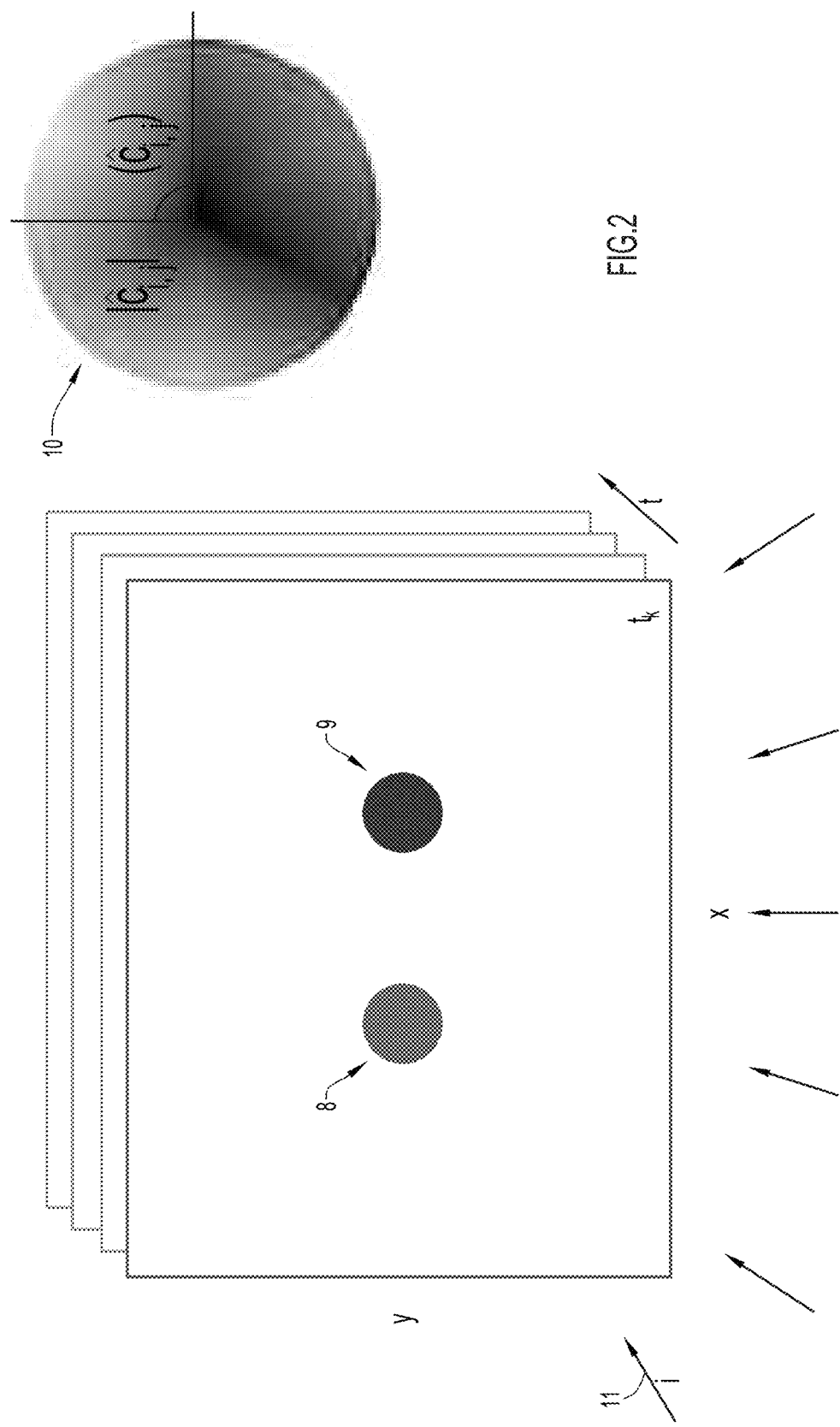
FIG. 2 illustrates simulated acquisition of complex-valued image projections to be used for spatiotemporal reconstruction of cardiac frequency angiographic phenomena in cross-sections of two simulated vessels, according to aspects of the present embodiments.

FIG. 2 illustrates the acquisition of complex-valued image projections with a simulated 2D cross-sectional image of two blood vessels for a series of time points. A fluoroscopic angiogram is generated by projecting x-rays through a 3D space to create a 2D projection image containing horizontal and vertical spatial data against an x-ray plate. However, this approach discards information (from 3D to 2D), which may be useful in understanding pathology of vessels. Present techniques provide an approach to reconstruct this 3D space, thereby, retrieving at least a portion of this discarded information. In this embodiment, angiographic images are obtained at faster than cardiac rate.

Thus, FIG. 2 shows a 2D slice of a 3D space comprising angiographic data. In this example, the image projection is a 1D spatial row of the 2D slice (plane) after x-ray projection. Thus, for each arrow (representing projected x rays), a corresponding 1D spatial row is generated. In one embodiment, the projection angles may be densely packed and vary across a half circle from 0 to $\pi$. Although demonstrated for a 1D image projection of a 2D slice, these techniques, including the inverse Penrose transform or Penrose back projection technique, may be extended to 3D by repeating the operations demonstrated herein. For example, a sequence of 2D image projections may be used to generate a 3D object.

Two vessels ("vessel 1" 8 and "vessel 2" 9) are shown in FIG. 2. In this example, every pixel in the computer generated image represents a complex-valued datum. Each complex valued datum c is rendered with a brightness-hue color model, where cardiac frequency magnitude is rendered as brightness, and phase is rendered as hue, for example, according to the legend brightness-hue legend 10.

The two spatial dimensions of this illustration, x and y, are complemented by the time dimension t to represent a time sequence. In a spatiotemporal reconstruction of cardiac frequency angiography phenomena, the spatiotemporal reconstruction has a cine character with a time dimension. A pulse wave at cardiac frequency cycles through the hues as shown in the brightness-hue legend 10.

In some aspects, all pixels in an angiographic image are indexed to an index source varying at cardiac frequency. In some aspects, the index source may originate outside the organ being imaged. An example would be a cardiac signal obtained from a pulse oximeter or other suitable source. Alternately, it may originate from within the image. An example would be a well-defined ROI in a blood vessel. Because of physiological coherence, after indexing, there is a relative variation in phase (e.g., rendered as hue) in each pixel from an angiographic image frame at a time $t_k$ to another frame at another time $t_{k+1}$. In some embodiments, angiographic data that is obtained and based on different heartbeats may be combined based on indexing to the index source.

While this example is shown using a single time point ($t_k$), present techniques may be applied to a sequence of images (e.g., 2D slices as a function of time ($t_{k+1}$), etc.) to show spatiotemporal reconstruction as a function of time.

This example illustrates the Penrose back projection/inverse Penrose transform with a relatively large number of x-ray projections, which after transformation, appears smooth. However, present techniques are applicable to sparse data, e.g., using constrained back projection techniques that operate with few projections. In embodiments, interpolation may be used to smooth results obtained from sparse angiographic data. Thus, in another embodiment, x-ray projections may be relatively sparse in number.

The projection angles may be obtained in any suitable manner relative to any suitable device, including for example, devices that utilize parallel beam, fan beam, or cone beam geometry.

FIGS. 3A-3B illustrate the reconstruction of objects (e.g., in this case, vessels from FIG. 2) using a complex-valued field at a given time point from an inverse Penrose transform of complex-valued projections (e.g., to obtain the coherent objects of FIG. 2).

FIG. 3A shows a sinogram produced by the x-ray projections shown in FIG. 2, wherein the horizontal axis represents an angiographic projection angle and the vertical axis corresponds to a spatial dimension based on the horizontal spatial dimension of the objects represented in FIG. 2. In embodiments, the sinogram may be generated by a set of x-ray machines obtaining angiograms with reference to the same cardiac cycle. Alternatively, the sinogram may be generated by one x-ray machine obtaining an angiogram that is synchronized to another x-ray machine by reference to the same cardiac signal.

Several 2D images that are not obtained at the same time may be synchronized based on a reference cardiac signal, which may be a pulse rate or a respiration rate. In this embodiment, two vessels may be pulsing at the same point in time relative to the reference cardiac signal. In this aspect, an angiogram at different positions may be obtained with a monoplane machine (gantry) that is changing positions relative to a subject/object. In this embodiment, the position of the gantry is known relative to the cardiac signal and to the object. Reconstruction of a 3D image from two or more monoplane image projections, may be performed based on an index source such as a cardiac signal (e.g., which may be different heartbeats) and identification of the pulse wave that is reconstructed.

In FIG. 3A, the complex-valued sinogram 12 undergoes a mathematical transform, e.g., the inverse Penrose transform 13, to yield a complex-valued reconstruction 14, as shown in FIG. 3B, representing the physiologically coherent objects (e.g., pulsing blood vessels) of FIG. 2. These objects may be rendered into an image, e.g., based on the brightness-hue model of cardiac frequency angiographic phenomena, based on magnitude and phase, which may optionally be rendered according to brightness-hue legend 10.

FIG. 2 and FIG. 3A-3B illustrate the present techniques at a single time point. The angiographic frame $t_k$ in FIG. 2 is but one of a sequence of frames obtained at faster than cardiac frequency as is required according to the Nyqvist sampling theorem to obtain a cine spatiotemporal reconstruction of a moving vascular pulse wave. The techniques illustrated by FIG. 2 and FIGS. 3A-3B may be repeated across the duration of the angiographic bolus to produce a plurality of sinograms like FIG. 3A that represent cardiac activity as indexed to an index source, such as a cardiac pacemaker. FIGS. 3A-3B illustrate object reconstruction from projections obtained using the angiographic methodology of FIG. 2. If the projections for each angiographic frame are in two spatial dimensions along with a time dimension, then the reconstructed cine object has three spatial dimensions and a time dimension.

Present techniques are illustrated with a series of two-dimensional simulated objects that produce a sequence of one-dimensional projections to be inverse Penrose transformed into a two-dimensional image representing the object. Similarly, 3D objects may be reconstructed from 2D image projections. Furthermore, these techniques apply to planar projections, fan beam projections, or cone beam projections.

Vascular coherence allows the use of reconstruction algorithms other than the inverse Penrose transform illustrated here. Examples of other reconstruction algorithms include but are not limited to filtered back projection, iterative methods, constrained or regularized methods, wavelet methods, expectation maximization methods, or maximum entropy methods. Furthermore, vascular coherence applies regardless of whether a reconstruction algorithm operates on finely spaced projections across a semicircle or sparsely spaced projections under a tomosynthesis strategy. Interpolation techniques may be utilized for sparsely spaced projections.

Physiological coherence at cardiac frequency permits flexibility in the orientation and timing of the projections. For example, projections may be obtained in sequence, in parallel, or in some combination thereof, such as by a continuously moving gantry. These approaches apply to any suitable imaging technique, including planar projections, fan beam projections, or cone beam projections.

Physiological coherence at cardiac frequency, while discovered in angiograms of human brain, applies to other organ systems and other vascular beds where there is pulse wave coherence at cardiac frequency.

Thus, a set of image projections obtained, for example, from angiographic machines that are capable of obtaining projections at different angles (e.g., at least two projections at right angles, or any other suitable angle) may be processed according to the techniques provided herein to generate cardiac frequency angiographic phenomena (including physiological coherence). Physiological coherence, which may appear as vascular pulse waves, may be utilized to reconstruct 3D objects, e.g., corresponding to the vascular pulse wave.

Figure 4A:
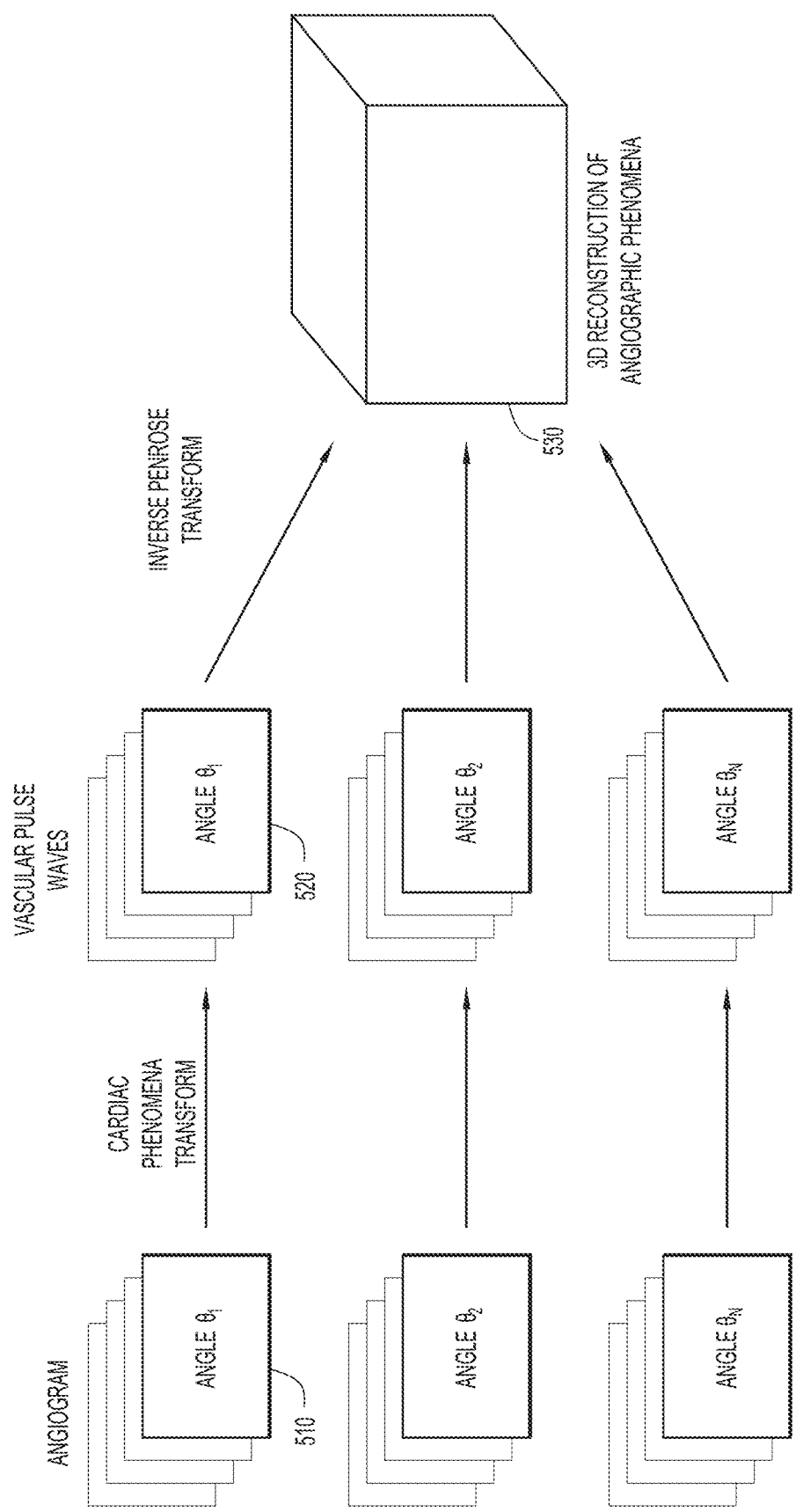
FIGS. 4A-4B show various aspects of spatiotemporal reconstruction, according to aspects of the present embodiments.

FIG. 4A shows an illustration of combining various angiograms to obtain a higher order spatiotemporal reconstruction, according to aspects of the present embodiments.

A series of angiograms 510, obtained at different angles is obtained at faster than cardiac frequency. Each set of angiographic data is processed, using a cardiac phenomena transform as described herein, to obtain cardiac frequency angiographic phenomena data 520, which may appear as vascular pulse waves.

The cardiac phenomena transform, referred to herein, refers to the processing techniques of the '761 patent, in which a mathematical transform, operable on complex data and retaining time indexing in the frequency domain, performs filtering at cardiac scale on the data in the frequency domain, and transforms the filtered data into the time domain using a corresponding inverse mathematical transform. The result is referred to as cardiac frequency angiographic phenomena.

The present application relies upon the disclosure provided in U.S. Pat. No. 10,123,761, which is incorporated herein by reference in its entirety, for the cardiac phenomena transform referenced herein comprising spatiotemporal reconstruction of vascular pulse waves by wavelet techniques within a two spatial dimensional angiographic projection.

Figure 8A:
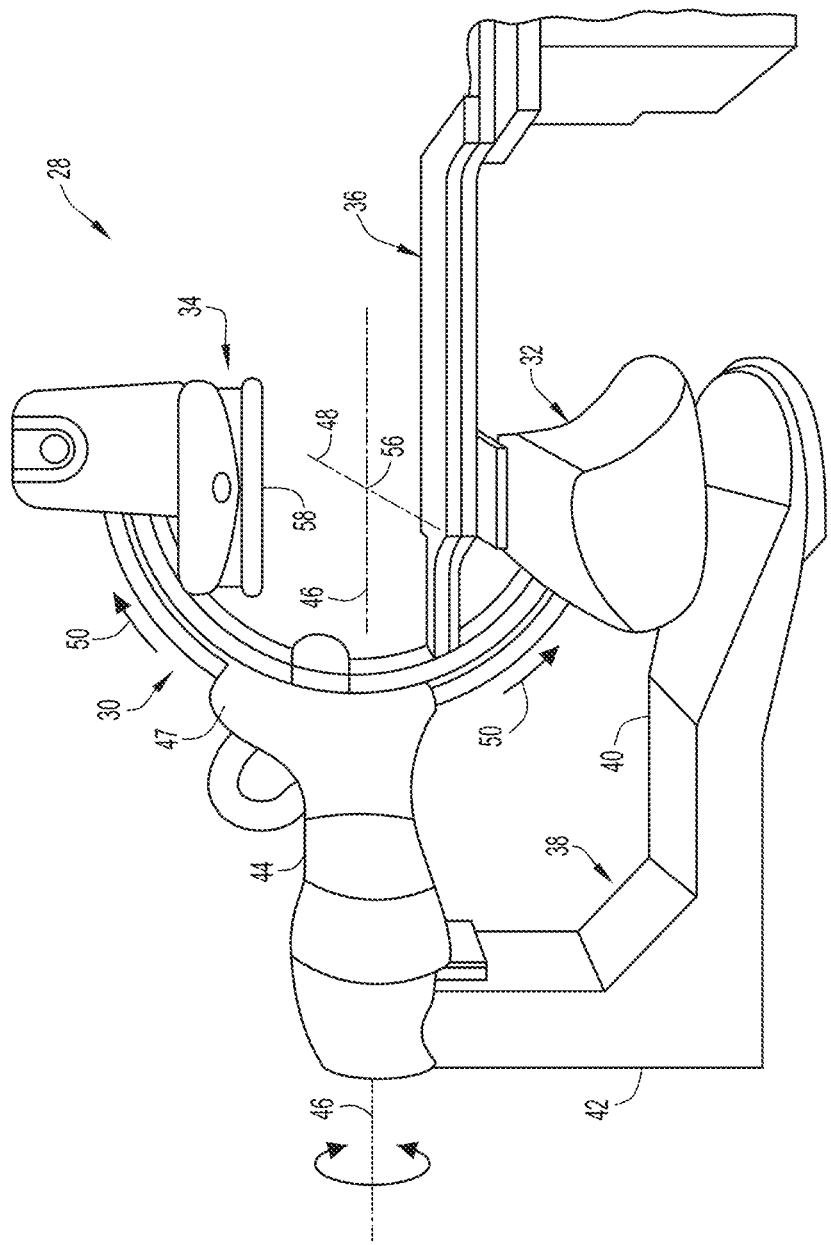
FIGS. 8A-8C depict x-ray systems that may be used for acquiring angiographic data, according to aspects of the present embodiments.
Figure 8B:
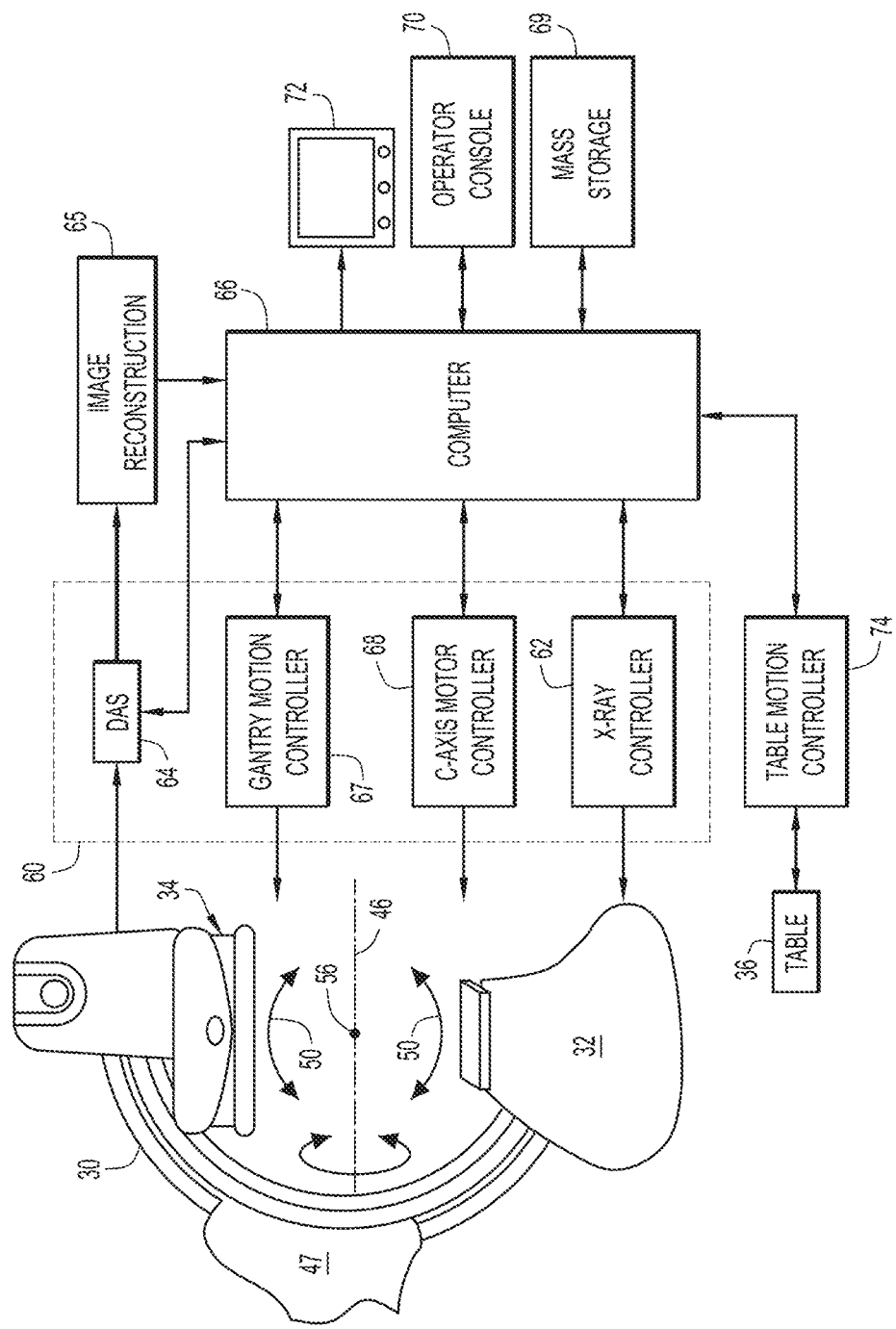
Figure 8C:
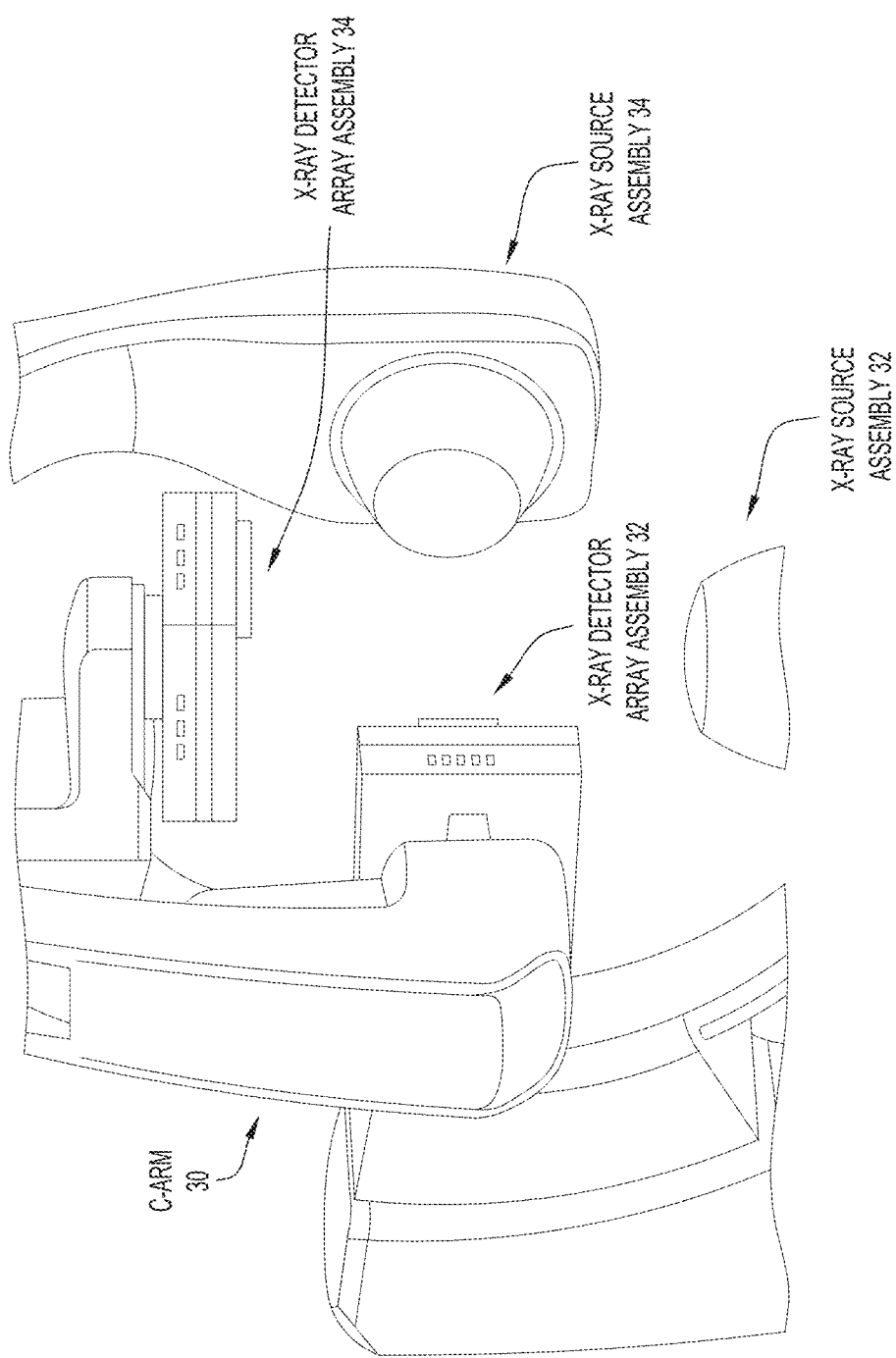

In carrying out the methods, systems, and computer program products provided herein, the angiographic data are recorded using a digital detector device, such as those commercially available as part of scanning devices available from manufacturers such as Philips and Siemens and/or as referenced in FIGS. 8A-8C. The digital data are then imported into a computer memory. After the import into computer memory of an angiogram, the spatiotemporal reconstruction of cardiac frequency angiographic phenomena may be obtained by the following operations (in the absence of motion alias):

the angiographic data consisting of n by m pixels by q frames data is imported into computer memory and reformatted with the processor in memory to give an n by m array of time signals each q samples long;

a complex valued wavelet transform is applied by the processor to each pixel-wise time signal, giving an n by m array of wavelet transforms;

the pixel-wise wavelet transforms are filtered for cardiac frequency by the processor. This is done by setting to zero all wavelet coefficients that do not correspond to cardiac wavelet scale (in the field of wavelets this term corresponds to the concept of cardiac frequency);

the pixel-wise wavelet transforms data are inverse wavelet transformed by the processor into time domain and reformatted in computer memory into q frames of n by m pixels. Each data element (voxel) in this three dimensional grid is a complex valued number;

each frame can be rendered as an image with a brightness hue color model to represent the complex datum in each pixel by the processor;

cardiac frequency magnitude is represented as brightness and phase as hue; and the q images may be rendered as motion cine by the processor or they may be stored as a video file format by the processor.

Any suitable transform, operable on complex numbers that retain time indexing after transformation into the frequency domain, and capable of extracting the spatiotemporal reconstruction of cardiac frequency angiographic phenomena is contemplated for use with the present techniques.

The cardiac frequency angiographic phenomena data (including vascular pulse waves) 520 may be processed, e.g., according to an inverse Penrose transform, to generate a higher order spatiotemporal reconstruction of the vascular pulse wave. Sequences corresponding to angle $\theta_1$, angle $\theta_2$, angle $\theta_N$ may be processed using an inverse Penrose transform (e.g., similar to FIGS. 3A-3B) to generate a 3D higher order object. Processing may be repeated for each set of frames, e.g., such that frames corresponding to angle $\theta_1$, angle $\theta_2$, angle $\theta_N$ may be processed using an inverse Penrose transform (for a determined angle at a given point in time). Here, it is assumed that each sequence comprising cardiac frequency angiographic phenomena has been synchronized, e.g., based on phase and/or magnitude of the cardiac frequency angiographic phenomena. In some aspects, interpolation may be used when aligning sequences of cardiac frequency angiographic phenomena. Thus, these techniques provide for visualization of a 3D vascular pulse wave as a function of time.

Synchronization may be performed by any suitable technique, including alignment based on phase and/or magnitude, and/or optionally and additionally, including a physiological marker. In some aspects, phase may be determined for each voxel, and alignment may be performed based on the computed phase.

Figure 4B:
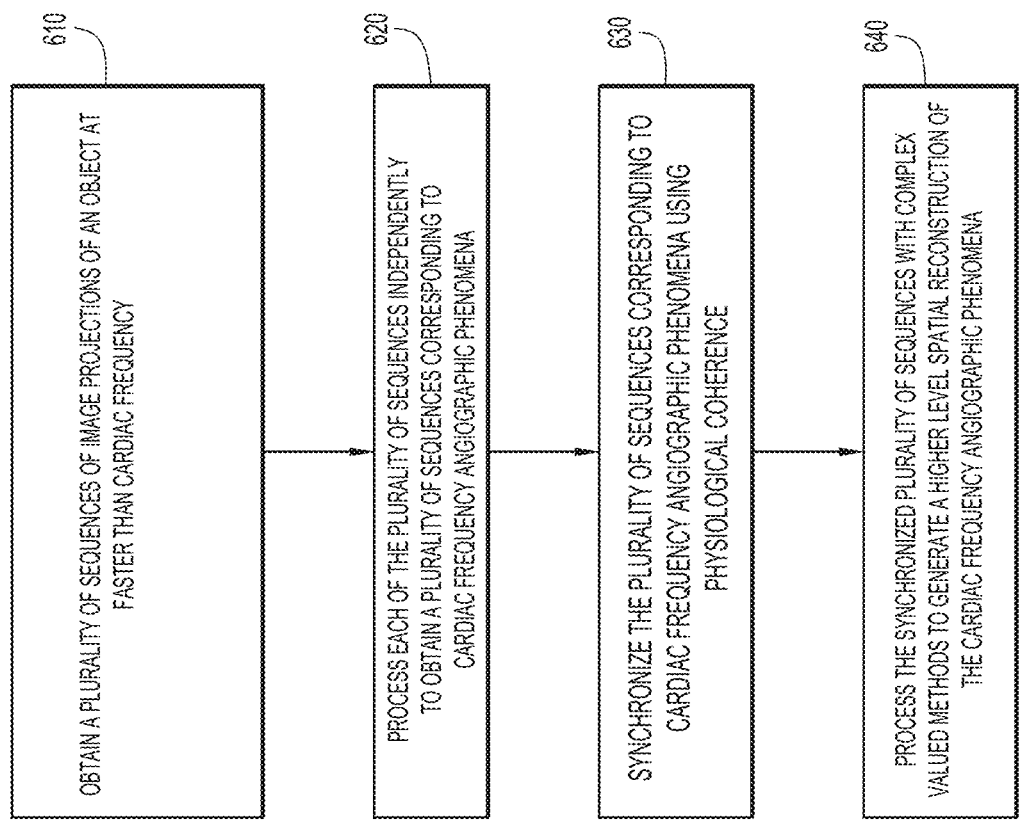

FIG. 4B shows a flow diagram of operations for spatiotemporal reconstruction, according to the techniques provided herein. At operation 610, a plurality of sequences of 2D image projections of a 3D object are obtained, each image projection associated with a respective angle of the orientation of the x-ray to an axis, wherein each sequence is obtained at faster than cardiac frequency. In aspects, the angiographic data may be obtained relative to an index source. At operation 620, each sequence of the plurality of sequences of 2D image projections is processed independently to obtain a plurality of sequences corresponding to cardiac frequency angiographic phenomena, represented as vascular pulse waves showing physiological coherence. At operation 630, the plurality of sequences corresponding to cardiac frequency angiographic phenomena are synchronized/aligned according to the techniques provided herein (e.g., phase and/or magnitude, etc.). The sequences may be indexed as described herein, as needed. At operation 640, the aligned plurality of sequences are inverse transformed, (e.g., sets of frames at different angles, aligned based on physiological coherence, are inverse transformed using, e.g., the inverse Penrose transform) to generate a 3D reconstruction of a vascular pulse wave.

Figure 5:
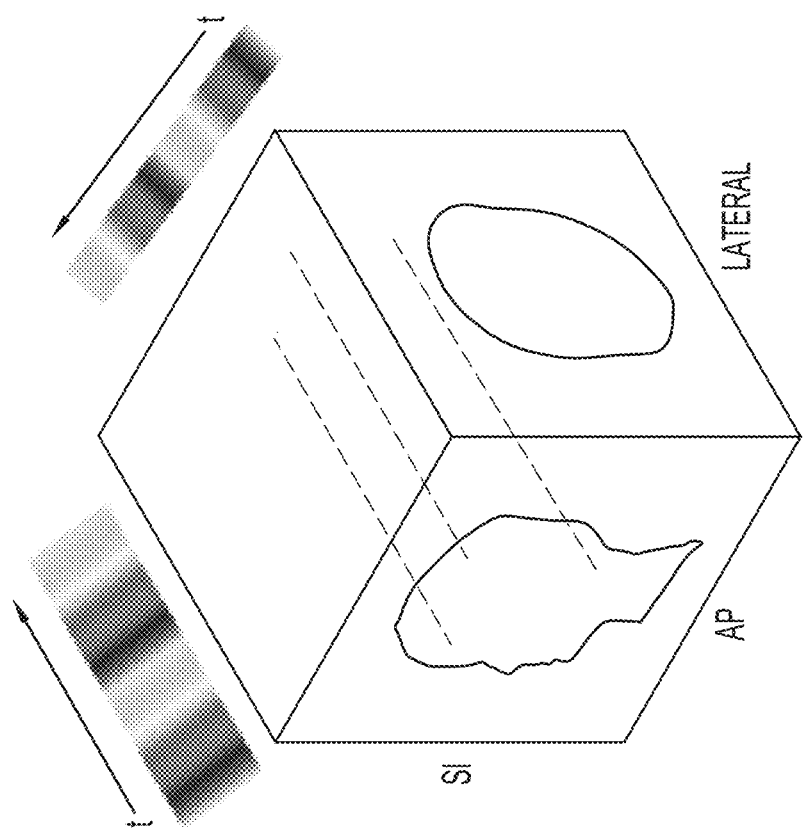
FIG. 5 shows a volumetric space generated for 3D spatial reconstruction of two dimensional projections using vascular coherence, according to aspects of the present embodiments.

Referring to FIG. 5, different sequences of projection images may be obtained at different angles, for example, by a biplane angiography device. Techniques may be employed to generate a 3D reconstruction from biplane projection images. In aspects, biplane devices obtain two dimensional images at different angles relative to a subject/object, wherein the images are obtained at the same point in time. Present techniques offer a way to utilize biplane technology in cardiac angiographic machines to obtain 3D reconstructed images, which may visualize the cardiac frequency angiographic phenomena.

In a conventional neurovascular x-ray angiogram, two image planes oriented at right angles are employed at the same time, e.g., using a biplane device, to obtain two simultaneous sequences of angiographic images for a single iodinated contrast injection. As an example case, and as shown in FIG. 5, two angiographic projections may be obtained and positioned in the anteroposterior (AP) and lateral planes. During image acquisition, the lateral plane and the anteroposterior plane may be obtained, and one or both sequences may be transposed or aligned relative to a volumetric space (e.g., a space with a SI axis, an AP axis, and a lateral axis). For example, the first sequence may be aligned relative to an anteroposterior plane, and the second sequence may be aligned relative to a lateral plane based on a 3D anatomic coordinate system, e.g., comprising 3 orthogonal axes, AP, superoinferior (SI), and right-left (lateral). In aspects, AP and lateral angiographic images obtained by a biplane system may be positioned to share the same SI axis (as shown in FIG. 5), such that a given object will have the same SI coordinate relative to both the AP and lateral projection images. Therefore, spatial matching from the AP and lateral projections may be employed to infer the spatial configuration of an anatomic structure in three dimensions. The spatial mismatch error is reduced by utilizing physiological coherence to perform the spatial matching. Thus, cardiac frequency angiographic phenomena (e.g., and in particular, the phase information) as extracted by the cardiac phenomena transform (e.g., wavelet angiography), allows reconstruction with reduced spatial mismatch error.

From a 2D perspective, different blood vessels in three dimensions may appear as overlapping in a two dimensional reconstruction. If two intersecting structures (vessels), with the same SI coordinate relative to an AP projection and a lateral projection, have different pulse wave phases after processing using a cardiac phenomena transform, these structures are unlikely to represent the same vascular structure (e.g., blood vessel).

If, on the other hand, these two structures share the same pulse wave phase, these structures likely represent the same vascular structure. Based on these techniques, a 3D spatial reconstruction may be obtained, by using phase information, or physiological coherence at cardiac frequency, to enhance spatial matching of structures from biplane projections. In some aspects, intersecting portions having the same pulse phase are retained, while other intersecting portions that have different phases are not retained. Accordingly, when reconstructing a 3D object from two dimensional images, vascular pulse waves may be used to identify a vessel in different images obtained at different orientations, based on the presence of synchronized pulsation in that vessel.

Conventional biplanar angiography is obtained and recorded, along with a cardiac reference signal. The cardiac phenomena transform is applied to each sequence of image projections to produce two 3D (2D spatial and time) spatiotemporal reconstructions. Each data element (voxel) is a complex-valued datum having a real and an imaginary component, which may be represented in polar form, wherein the magnitude expresses the strength of the cardiac frequency action at that voxel and the phase represents its relative position in the cardiac cycle.

The examples provided herein reference biplane coherence tomography at a single time point. However, present techniques may be extended to produce 4D biplane coherence tomography by processing a sequence of 3D (2D and time) image projections, and aggregating the results to generate a 4D (3D and time) biplane coherence tomogram.

Each projection is obtained by an angiographic device as a sequence of 2D spatial images. An AP projection and a lateral projection may be positioned such that the SI dimension for each projection is positioned on a vertical axis. According to present techniques, a 3D spatial volume (e.g., a cube, as shown in FIG. 5) is created by transposing/shifting one or more projections to be on a surface of a 3D spatial volume, wherein the 3D spatial volume is initially empty.

In aspects, each image projection (a plane) is replicated at a fixed interval along an axis. For example, the AP projection is replicated along the lateral axis and the lateral projection is replicated along the AP axis. Portions of the replicated images intersect in the volumetric space, and present techniques allow determination of which intersections are the same vessel and which are different vessels. For each voxel, a coherence value is determined. For a point intersecting with respect to the SI dimension, for a given pixel in the AP projection at a given lateral coordinate position, its complex conjugate is multiplied by all AP positions in the lateral projection, and the product, which is a complex number (a coherence metric) is stored at each voxel location. FIG. 5 shows example AP voxels replicated along the lateral dimension. (Although not shown, lateral pixels are also replicated along the AP dimension.)

Iterating by all SI, AP, and lateral coordinate positions results in population of the initially empty volume by voxels. In some aspects, voxels with smaller coherence values than a threshold are treated as transparent or discarded. Voxels with larger coherence values are considered to be the same vessel, and may be rendered with complex magnitude as brightness and phase as hue.

Relevant portions of processing operations are provided as follows. First, the data is read into memory, wherein the data comprises 3D (2D image projections and time) processed to generate cardiac frequency angiographic phenomena. In some aspects, data may be stored in a HDF 5 file format or any other suitable file format.

In some cases, it may be desirable to store complex-valued data separately as real and imaginary numbers. In this case, data may be read from each of the two files and combined pixel-wise into a single complex number:

Dimensions [biplanes=Import[biplaneFileName, {"Datasets", {"plane1", "plane2"}}]/. Association[Rule["Re", r_], Rule["Im", i_]]:→Complex[r, i]]

In some aspects, the data may be analyzed using quantile information to understand frequency and magnitude aspects of the data. This information may be used to guide rendering of the 3D reconstructed spatial data, e.g., allowing filtering, scaling or other normalization techniques to be used, if needed.

Image projections are transposed, as needed, to align SI dimensions (or other suitable dimensions) and allow AP and lateral dimensions to remain orthogonal, as shown in FIG. 5. Once aligned, each image projection is replicated at a predetermined interval along the other orthogonal spatial dimension. Thus, the AP image projection is replicated along the lateral axis, and the lateral image projection is replicated along the AP axis. In aspects, commands to replicate and transpose an image projection include:

Dimensions[vol2=Transpose[ConstantArray[biplanes [[2]], nelem], 1↔3]]

In some cases, the SI dimension of the first projection may not align with the SI dimension of the second projection, and the first or second position may be need to shifted, such that anatomical features of each projections align. This may occur if the bi-pane arms are not perfectly calibrated and rigidly fixed. Present techniques include determining a measure of alignment, and shifting an image projection by a suitable amount to maximize alignment.

To determine whether vessels intersect, a measure of coherence may be determined. In some aspects, a cutoff value, such as a threshold value (e.g., absolute value less than 0.89) may be set. Voxels falling within this range (low coherence) are set to a value of 0. In this case, a mathematical function that may be used is:

Dimensions[cvol=MapThread[corrComplex[#1, #2] &, {RotateRight[vol1/. q_Complex/; Abs[q] <1.→Complex[0., 0.], {0, shift, 0}], vol2/. q_Complex/; Abs[q] <.89→Complex[0., 0.]}, 3]] ]={128, 128, 128} wherein a correlation function is:

corrComplex[a_Complex, b_Complex]:=Block[{mag, phase},
mag=Max[Dot[ReIm[a], ReIm[b]], 0.];
phase=Arg[Mean[{a, b}]];
Complex[mag*Cos[phase], mag*Sin[phase]]]

In other aspects, a 3D spatial stack of complex images may be created, wherein each pixel has a brightness corresponding to cardiac frequency magnitude and a hue corresponding to cardiac frequency phase.

Dimensions[cimgvol=complexImage/@ (cvol[[10;; 110, 10;; 110, 10;; 110]])] ]={101}Image3D[cimgvol]

Figure 6:
FIG. 6 shows a spatiotemporal reconstruction relative to the volumetric space of FIG. 5, wherein the angiographic data was obtained using a biplane angiography device, according to aspects of the present embodiments.

The output is shown in FIG. 6, which is a 3D rendering of reconstructed biplane angiographic data.

Figure 7:
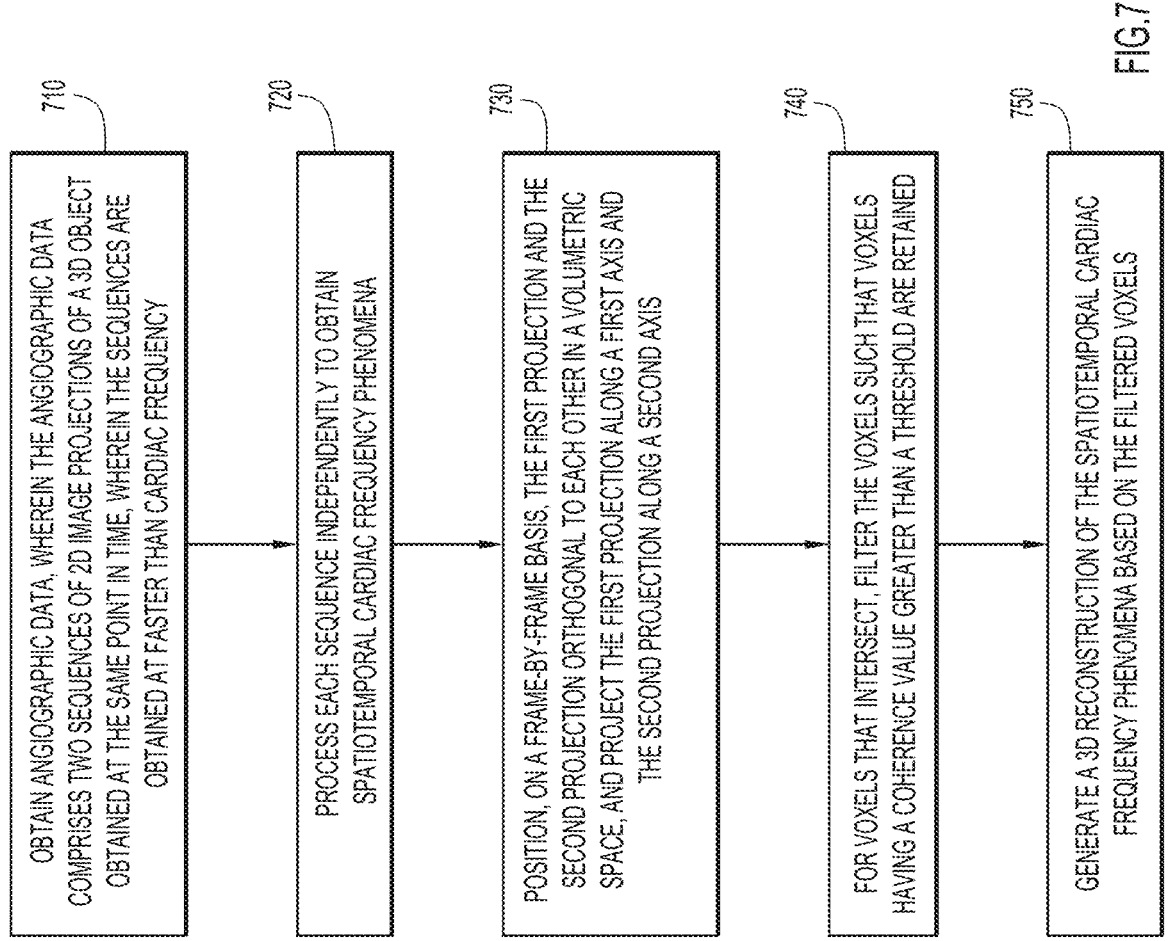
FIG. 7 is a flowchart of operations for spatiotemporal reconstruction of angiographic data obtained from a biplane angiography device, according to aspects of the present embodiments.

FIG. 7 shows high level operations for generating a 3D reconstruction based on biplane angiographic data. At operation 710, angiographic data is obtained, wherein the angiographic data comprises two sequences of 2D image projections of a 3D object obtained at the same point in time, wherein the sequences are obtained at faster than cardiac frequency. At operation 720, each sequence is processed independently to obtain spatiotemporal cardiac frequency phenomena. At operation 730, on a frame-by-frame basis (temporally aligned), the first and second projections are positioned in a volumetric space orthogonal to each other. The first sequence is projected along a first axis orthogonal to the second projection and the second sequence is projected along a second axis orthogonal to the first projection, wherein both the first and second sequences share a common third axis. At operation 740, for voxels that intersect in the volumetric space, the voxels are filtered such that voxels having a coherence value greater than a threshold are retained. At operation 750, a 3D reconstruction of the spatiotemporal cardiac frequency phenomena is generated based on the filtered voxels.

These techniques offer the ability to generate 3D spatial cardiac angiograms, a feature which is not available using conventional cardiac imaging techniques. Additionally, present techniques are compatible with biplane angiographic machines. Conventional angiography (monoplane cardiac angiography) is not performed with biplane machines, and present techniques offer an improvement in cardiac angiograms imaging.

Present techniques provide the ability to visualize physiological coherence (including vascular pulse waves), in individual 2D slices as well as in 3D. Further, present techniques may be used to show the distribution of vascular pulsations in 3D dimensions over a 3D structure, such as the ventricles of the brain or to show the vascular pulsations across the muscles of a beating heart.

Referring to FIGS. 8A-8C, an x-ray system 28 is illustrated that may be employed for obtaining an angiogram at a faster than cardiac rate, such as via fluoroscopic angiography. As previously described, in acquiring an angiograph, a chemical contrast agent is injected into the patient that allows image projections to be captured by the x-ray system as a two-dimensional image projection. An angiographic study or angiographic data comprises a sequence (e.g., as a function of time) of these two dimensional projection images, with the angiographic image frames acquired at faster than cardiac frequency to allow spatiotemporal reconstruction of the cardiac frequency phenomena, e.g., into a cardiac space angiogram.

As shown in FIG. 8A, the rotational x-ray system 28 is characterized by a gantry having a C-arm 30 which carries an x-ray source assembly 32 on one of its ends and an x-ray detector array assembly 34 at its other end. The gantry enables the x-ray source 32 and detector 34 to be oriented in different positions and angles around a patient disposed on a table 36, while enabling a physician access to the patient. The gantry includes a pedestal 38 which has a horizontal leg 40 that extends beneath the table 36 and a vertical leg 42 that extends upward at the end of the horizontal leg 40 that is spaced from of the table 36. A support arm 44 is rotatably fastened to the upper end of vertical leg 42 for rotation about a horizontal pivot axis 46.

The pivot axis 46 is aligned with the centerline of the table 36, and the arm 44 extends radially outward from the pivot axis 46 to support a C-arm drive assembly 47 on its outer end. The C-arm 30 is slidably fastened to the drive assembly 47 and is coupled to a drive motor (not shown) which slides the C-arm 30 to revolve it about a C-axis 48 as indicated by arrows 50. The pivot axis 46 and C-axis 48 intersect each other, at an isocenter 56 located above the table 36, and are perpendicular to each other.

The x-ray source assembly 32 is mounted to one end of the C-arm 30 and the detector array assembly 34 is mounted to its other end. The x-ray source 32 emits a beam of x-rays which are directed at the detector array 34. Both assemblies 32 and 34 extend radially inward to the pivot axis 46 such that the center ray of this beam passes through the system isocenter 56. The center ray of the beam thus can be rotated about the system isocenter around either the pivot axis 46 or the C-axis 48, or both, during the acquisition of x-ray attenuation data from a subject placed on the table 36.

The x-ray source assembly 32 contains an x-ray source which emits a beam of x-rays when energized. The center ray passes through the system isocenter 56 and impinges on a two-dimensional flat panel digital detector 58 housed in the detector assembly 34. The detector 58 may be, for example, a 2048×2048 element two-dimensional array of detector elements. Each element produces an electrical signal that represents the intensity of an impinging x-ray and hence the attenuation of the x-ray as it passes through the patient. During a scan, the x-ray source assembly 32 and detector array assembly 34 are rotated about the system isocenter 56 to acquire x-ray attenuation projection data from different angles. The detector array is able to acquire at least about 50 projections or more, or views, per second which is the limiting factor that determines how many views can be acquired for a prescribed scan path and speed.

Referring to FIG. 8B, the rotation of the assemblies 32 and 34 and the operation of the x-ray source are governed by a control mechanism 60 of the x-ray system. The control mechanism 60 includes an x-ray controller 62 that provides power and timing signals to the x-ray source 32. A data acquisition system (DAS) 64 in the control mechanism 60 samples data from detector elements and passes the data to an image reconstructor 65. The image reconstructor 65 receives digitized x-ray data from the DAS 64 and performs high speed image reconstruction according to the methods of the present disclosure. The reconstructed image is applied as an input to a computer 66 which stores the image in a mass storage device 69 or processes the image further.

The control mechanism 60 also includes gantry motor controller 67 and a C-axis motor controller 68. In response to motion commands from the computer 66, the motor controllers 67 and 68 provide power to motors in the x-ray system that produce the rotations about respective pivot axis 46 and C-axis 48. The computer 66 also receives commands and scanning parameters from an operator via console 70 that has a keyboard and other manually operable controls. An associated display 72 allows the operator to observe the reconstructed image and other data from the computer 66. The operator supplied commands are used by the computer 66 under the direction of stored programs to provide control signals and information to the DAS 64, the x-ray controller 62 and the motor controllers 67 and 68. In addition, computer 66 operates a table motor controller 74 which controls the motorized table 36 to position the patient with respect to the system isocenter 56.

Referring to FIG. 8C, a biplane angiographic device is shown, with two x-ray detector array assemblies 34 and two x-ray source assemblies 32. This device may be used with embodiments of the biplane angiogram device referenced herein. This device is operated in a similar manner as the device in FIGS. 8A and 8B. In some aspects, the biplane angiographic device may obtain images along different axes at the same point in time.

Figure 9:
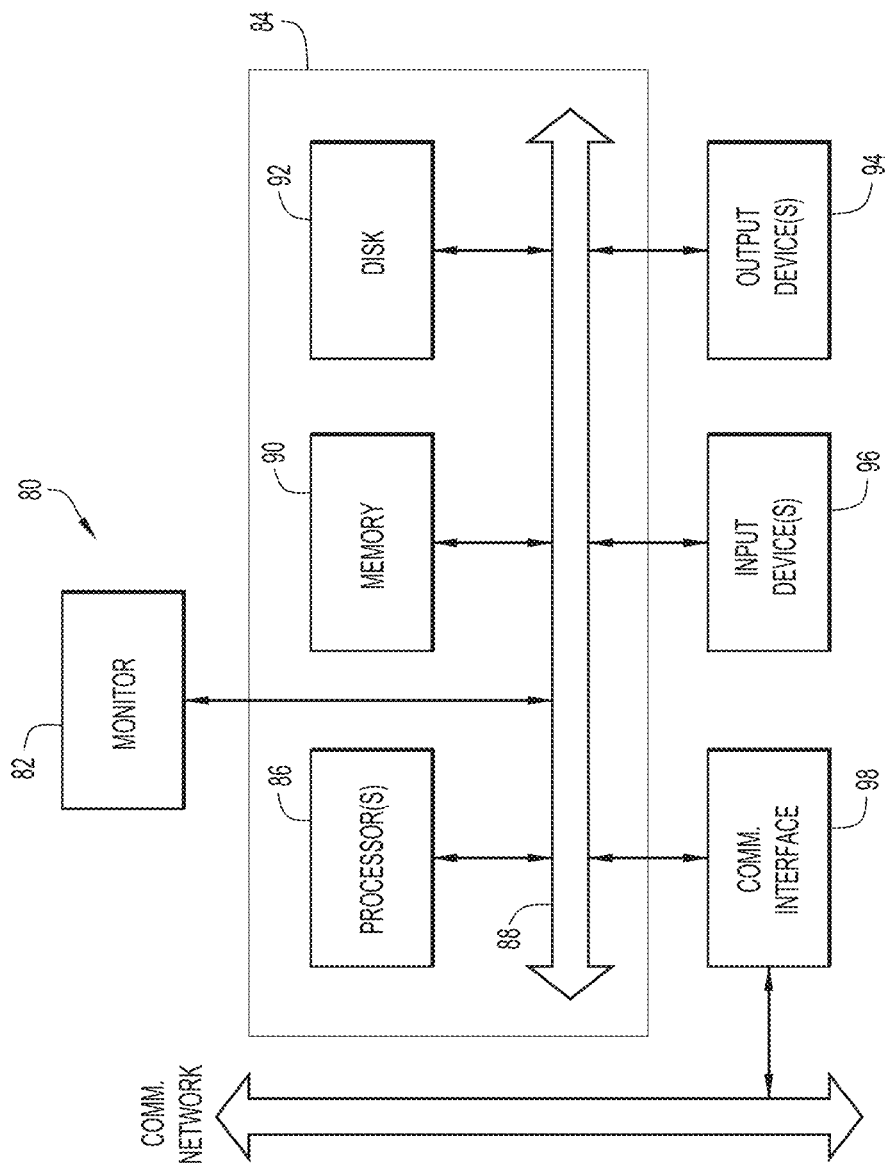
FIG. 9 is a block diagram of a computer system or information processing device that may be used with embodiments of the invention, according to aspects of the present embodiments.

Referring now to FIG. 9, a block diagram of a computer system or information processing device 80 is illustrated that may be used with rotational x-ray system 28 of FIGS. 8A-8C for the extraction of cardiac frequency phenomena and the use of angiographic coherence at cardiac frequency to synchronize separate projections of reconstructed spatiotemporal cardiac frequency phenomena and/or to reconstruct a higher dimensional cine representation of spatiotemporal cardiac frequency phenomena from a plurality of lower dimensional synchronized projections of reconstructed spatiotemporal cardiac frequency phenomena, according to an embodiment of the present invention.

FIG. 9 is illustrative of a general-purpose computer system 80 programmed according to techniques within this disclosure or a specific information processing device for the embodiments provided herein, and is not intended to limit the scope of the subject matter disclosed herein. One of ordinary skill in the art would recognize other variations, modifications, and alternatives to computer system 80 that remain within the scope and equivalents of the disclosure.

In one embodiment, computer system 80 includes monitor 82, computer 84 (which includes processor(s) 86, bus subsystem 88, memory subsystem 90, and disk subsystem 92), user output devices 94, user input devices 96, and communications interface 98. Monitor 82 can include hardware and/or software elements configured to generate visual representations or displays of information. Some examples of monitor 82 may include familiar display devices, such as a television monitor, a cathode ray tube (CRT), a liquid crystal display (LCD), or the like. In some embodiments, monitor 82 may provide an input interface, such as incorporating touch screen technologies.

Computer 84 can include familiar computer components, such one or more central processing units (CPUs), memories or storage devices, graphics processing units (GPUs), communication systems, interface cards, or the like. As shown in FIG. 9, computer 84 may include one or more processor(s) 86 that communicate with a number of peripheral devices via bus subsystem 88. Processor(s) 86 may include commercially available central processing units or the like. Bus subsystem 88 can include mechanisms for letting the various components and subsystems of computer 84 communicate with each other as intended. Although bus subsystem 88 is shown schematically as a single bus, alternative embodiments of the bus subsystem may utilize multiple bus subsystems. Peripheral devices that communicate with processor(s) 86 may include memory subsystem 90, disk subsystem 92, user output devices 94, user input devices 96, communications interface 98, or the like.

Memory subsystem 90 and disk subsystem 92 are examples of physical storage media configured to store data. Memory subsystem 90 may include a number of memories including random access memory (RAM) for volatile storage of program code, instructions, and data during program execution and read only memory (ROM) in which fixed program code, instructions, and data are stored. Disk subsystem 92 may include a number of file storage systems providing persistent (non-volatile) storage for programs and data. Other types of physical storage media include floppy disks, removable hard disks, optical storage media such as CD-ROMS, DVDs and bar codes, semiconductor memories such as flash memories, read-only-memories (ROMS), battery-backed volatile memories, networked storage devices, or the like.

Memory subsystem 90 and disk subsystem 92 may be configured to store programming and data constructs that provide functionality or features of techniques discussed herein. Software code modules and/or processor instructions that when executed by processor(s) 86 implement or otherwise provide the functionality may be stored in memory subsystem 90 and disk subsystem 92.

User input devices 94 can include hardware and/or software elements configured to receive input from a user for processing by components of computer system 80. User input devices can include all possible types of devices and mechanisms for inputting information to computer system 84. These may include a keyboard, a keypad, a touch screen, a touch interface incorporated into a display, audio input devices such as microphones and voice recognition systems, and other types of input devices. In various embodiments, user input devices 94 can be embodied as a computer mouse, a trackball, a track pad, a joystick, a wireless remote, a drawing tablet, a voice command system, an eye tracking system, or the like. In some embodiments, user input devices 94 are configured to allow a user to select or otherwise interact with objects, icons, text, or the like that may appear on monitor 82 via a command, motions, or gestures, such as a click of a button or the like.

User output devices 96 can include hardware and/or software elements configured to output information to a user from components of computer system 80. User output devices can include all possible types of devices and mechanisms for outputting information from computer 84. These may include a display (e.g., monitor 82), a printer, a touch or force-feedback device, audio output devices, or the like.

Communications interface 98 can include hardware and/or software elements configured to provide unidirectional or bidirectional communication with other devices. For example, communications interface 98 may provide an interface between computer 84 and other communication networks and devices, such as via an internet connection.

FIG. 9 is representative of a computer system capable of embodying embodiments of the present invention. It will be readily apparent to one of ordinary skill in the art that many other hardware and software configurations are suitable for use with the present invention. For example, the computer may be a desktop, portable, rack-mounted or tablet configuration. Additionally, the computer may be a series of networked computers. In still other embodiments, the techniques described above may be implemented upon a chip or an auxiliary processing board.

It will thus be seen that the objects set forth above, among those made apparent from the preceding description, are efficiently attained and, because certain changes may be made in carrying out the above method and in the construction(s) set forth without departing from the spirit and scope of aspects of the invention, it is intended that all matter contained in the above description and shown in the accompanying drawings shall be interpreted as illustrative and not in a limiting sense.

The following claims are intended to cover all of the generic and specific features of the objects of the invention herein described and all statements of the scope thereof which, as a matter of language, might be said to fall there-between.

What is claimed is:

1. A method for angiography comprising:
    reconstructing a higher dimensional cine representation of spatiotemporal cardiac frequency phenomena from a plurality of lower dimensional synchronized projections of reconstructed spatiotemporal cardiac frequency phenomena obtained at faster than cardiac frequency, wherein the reconstruction is performed using physiological coherence at cardiac frequency in the spatiotemporal reconstructions of angiographic phenomena, and wherein complex valued methods are used for operating on the projections.

2. A method for reconstructing a higher dimensional spatial representation of spatiotemporal cardiac frequency phenomena from a plurality of lower dimensional image projections, obtained using angiography, comprising:
    obtaining a plurality of sequences of image projections of an object at faster than cardiac frequency;
    processing each of the plurality of sequences independently to obtain a plurality of sequences corresponding to cardiac frequency angiographic phenomena;
    synchronizing the plurality of sequences corresponding to cardiac frequency angiographic phenomena using physiological coherence; and
    processing the synchronized plurality of sequences with complex valued methods to generate a higher level spatial reconstruction of the cardiac frequency angiographic phenomena.

3. The method of claim 2, wherein the complex-valued method is an inverse Penrose transform.

4. The method of claim 2, wherein the sequences comprise sparse data.

5. The method of claim 4, wherein interpolation is used to augment processing of the sparse data.

6. The method of claim 2, wherein types of angiography include parallel beam geometry, fan beam geometry, or cone beam geometry.

7. The method of claim 2, wherein the plurality of sequences are obtained with reference to an index source.

8. The method of claim 7, wherein the index source is obtained from a physiological marker, a pulse oximeter, an electrocardiogram, or an intracranial pressure waveform.

9. The method of claim 2, wherein:
    a 3D reconstruction is generated from a plurality of 2D image projections, or
    a 2D reconstruction is generated from a plurality of 1D image projections.

10. A computer system for angiography comprising:
    one or more computer processors;
    one or more computer readable storage media;
    program instructions stored on the one or more computer readable storage media for execution by at least one of the one or more computer processors, the program instructions comprising executable instructions to:
    reconstruct a higher dimensional cine representation of spatiotemporal cardiac frequency phenomena from a plurality of lower dimensional synchronized projections of reconstructed spatiotemporal cardiac frequency phenomena obtained at faster than cardiac frequency, wherein the reconstruction is performed using physiological coherence at cardiac frequency in the spatiotemporal reconstructions of angiographic phenomena, and wherein complex valued methods are used for operating on the projections.

11. The system of claim 10, wherein the complex-valued method is an inverse Penrose transform.

12. The system of claim 10, wherein the processor is further configured to control an angiography device for parallel beam geometry, fan beam geometry, or cone beam geometry.

13. The system of claim 10, wherein the processor is further configured to obtain the projections with reference to an index source.

14. The system of claim 13, wherein the index source is obtained from a physiological marker, a pulse oximeter, an electrocardiogram, or an intracranial pressure waveform.

15. A computer program product for angiography comprising a non-transitory computer readable storage medium having program instructions embodied therewith, the program instructions executable by a computer to cause the computer to process instructions to:
    reconstruct a higher dimensional cine representation of spatiotemporal cardiac frequency phenomena from a plurality of lower dimensional synchronized projections of reconstructed spatiotemporal cardiac frequency phenomena obtained at faster than cardiac frequency, wherein the reconstruction is performed using physiological coherence at cardiac frequency in the spatiotemporal reconstructions of angiographic phenomena, and wherein complex valued methods are used for operating on the projections.

16. The computer program product of claim 15, wherein the complex-valued method is an inverse Penrose transform.

17. The computer program product of claim 15, wherein the program instructions are operable to be executed on an angiography device for parallel beam geometry, fan beam geometry, or cone beam geometry.

18. The computer program product of claim 15, wherein the program instructions are configured to obtain the projections with reference to an index source.

19. The computer program product of claim 18, wherein the index source is obtained from a physiological marker, a pulse oximeter, an electrocardiogram, or an intracranial pressure waveform.

* * * * *